United States Patent
Hu et al.

(10) Patent No.: US 10,577,424 B1
(45) Date of Patent: Mar. 3, 2020

(54) ANTIBODIES BINDING VISTA AND USES THEREOF

(71) Applicant: Beijing Mabworks Biotech Co.Ltd, Beijing (CN)

(72) Inventors: Wenqi Hu, Las Vegas, NV (US); Jiangmei Li, Beijing (CN); Feng Li, Beijing (CN)

(73) Assignee: Beijing Mabworks Biotech Co., Ltd., Beijing (CN)

( * ) Notice: Subject to any disclaimer, the term of this patent is extended or adjusted under 35 U.S.C. 154(b) by 0 days.

(21) Appl. No.: 16/541,193

(22) Filed: Aug. 15, 2019

(51) Int. Cl.
| | |
|---|---|
| *A61K 39/395* | (2006.01) |
| *C07K 16/18* | (2006.01) |
| *C07K 16/28* | (2006.01) |
| *C07K 16/30* | (2006.01) |
| *A61K 45/06* | (2006.01) |
| *A61P 35/00* | (2006.01) |
| *C07K 14/435* | (2006.01) |
| *C07K 14/705* | (2006.01) |
| *A61K 39/00* | (2006.01) |

(52) U.S. Cl.
CPC ...... *C07K 16/2827* (2013.01); *A61K 39/3955* (2013.01); *A61K 39/39558* (2013.01); *A61K 45/06* (2013.01); *A61P 35/00* (2018.01); *C07K 16/28* (2013.01); *A61K 2039/505* (2013.01); *A61K 2039/507* (2013.01); *C07K 16/18* (2013.01); *C07K 16/2803* (2013.01); *C07K 2317/24* (2013.01); *C07K 2317/31* (2013.01); *C07K 2317/56* (2013.01); *C07K 2317/565* (2013.01); *C07K 2317/76* (2013.01); *C07K 2317/92* (2013.01)

(58) Field of Classification Search
CPC .......... A61K 2039/505; A61K 39/3955; A61K 2039/507; A61K 39/0011; A61K 39/395; A61K 39/39558; A61K 39/39533; C07K 2317/24; C07K 2317/33; C07K 2317/565; C07K 2317/56; C07K 16/28; C07K 16/18; C07K 16/30

See application file for complete search history.

(56) References Cited

U.S. PATENT DOCUMENTS

| | | | | |
|---|---|---|---|---|
| 2016/0083472 A1* | 3/2016 | Noelle | ............... | A61K 45/06 424/134.1 |
| 2017/0051061 A1* | 2/2017 | Snyder | ............... | C07K 16/3038 |
| 2017/0233479 A1* | 8/2017 | Snyder | ............. | G01N 33/57423 424/174.1 |
| 2018/0306799 A1* | 10/2018 | Snyder | ............. | G01N 33/57492 |

OTHER PUBLICATIONS

Blando et al. Comparison of immune infiltrates in melanoma and pancreatic cancer highlights VISTA as a potential target in pancreatic cancer. Proc Natl Acad Sci USA 116(5): 1692-1697, 2019.*
Boger et al. The novel checkpoint regulator VISTA is expressed in gastric carcinoma and associated with PD-L1/PD-1: a future perspective fora combined gastric cancer therapy? Oncolmmunol 6: 4, e 1293215 (9 total pages).*
Deng et al. A new VISTA on combination therapy for negative checkpoint regulator blockade. J Immunotherap Cancer 4: 86, 2016 (7 total pages).*
Gabrilovich et al. Coordinated regulation of myeloid cells by tumours. Nature Rev 12: 253-268, 2012.*
Le Mercier et al. VISTA regulates the development of protective antitumor immunity. Cancer Res 74(7): 1933-1944, 2014.*
Lines et al. VISTA is a novel broad-spectrum negative checkpoint regulator for cancer immunotherapy. Cancer Immunol Res 2(6): 510-517, 2014.*
Mulati et al. VISTA expressed in tumour cells regulates T cell function. Brit J Cancer 120: 115-127, 2019.*
Nowak et al. Immunoregulatory functions of VISTA. Immunol Rev 276: 66-79, 2017.*

* cited by examiner

*Primary Examiner* — Bridget E Bunner
(74) *Attorney, Agent, or Firm* — Duane Morris LLP

(57) ABSTRACT

An isolated monoclonal antibody or the antigen binding portion thereof that specifically binds human VISTA. A nucleic acid molecule encoding the antibody, an expression vector, a host cell and a method for expressing the antibody or the antigen binding portion thereof are also provided. The present disclosure further provides a bispecific molecule, and a pharmaceutical composition comprising the antibody or the binding moieties thereof, as well as a treatment method using an anti-VISTA antibody or the antigen binding portion thereof of the present disclosure.

19 Claims, 7 Drawing Sheets
Specification includes a Sequence Listing.

A

B

A CD3/Vehicle 
B CD8/Vehicle 
C CD4/Vehicle 
D CD3/161E5VH2VL3 
E CD8/161E5VH2VL3 
F CD4/161E5VH2VL3

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: VH-CDR1 for mouse, chimeric and humanized 161E5
      antibodies

<400> SEQUENCE: 1

Asp Tyr Tyr Ile Asn
1               5

<210> SEQ ID NO 2
<211> LENGTH: 17

-continued

```
<212> TYPE: PRT
<213> ORGANISM: Artificial Sequence
<220> FEATURE:
<223> OTHER INFORMATION: VH-CDR2 for mouse, chimeric and humanized 161E5
      antibodies

<400> SEQUENCE: 2

Arg Ile Phe Pro Gly Ser Gly Asn Ala Tyr Tyr Asn Glu Lys Phe Lys
1               5                   10                  15

Asp

<210> SEQ ID NO 3
<211> LENGTH: 12
<212> TYPE: PRT
<213> ORGANISM: Artificial Sequence
<220> FEATURE:
<223> OTHER INFORMATION: VH-CDR3 for mouse, chimeric and humanized 161E5
      antibodies

<400> SEQUENCE: 3

Asp Asp Ser Phe Tyr Gly Tyr Trp Tyr Phe Asp Val
1               5                   10

<210> SEQ ID NO 4
<211> LENGTH: 17
<212> TYPE: PRT
<213> ORGANISM: Artificial Sequence
<220> FEATURE:
<223> OTHER INFORMATION: VL-CDR1 for mouse, chimeric and humanized 161E5
      antibodies

<400> SEQUENCE: 4

Lys Ser Ser Gln Ser Val Leu Tyr Ser Ser Asn Gln Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: VL-CDR2 for mouse, chimeric and humanized 161E5
      antibodies

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: VL-CDR3 for mouse, chimeric and humanized 161E5
      antibodies

<400> SEQUENCE: 6

His Gln Tyr Leu Ser Ser Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: VH for mouse and chimeric 161E5 antibodies
```

<400> SEQUENCE: 7

```
Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Ser Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Phe Pro Gly Ser Gly Asn Ala Tyr Tyr Asn Glu Lys Phe
    50                  55                  60

Lys Asp Lys Ala Thr Leu Thr Val Glu Lys Ser Ser Ala Ala Tyr
65                  70                  75                  80

Met Gln Leu Ser Ser Leu Thr Ser Glu Asp Ser Ala Val Tyr Phe Cys
                85                  90                  95

Ala Arg Asp Asp Ser Phe Tyr Gly Tyr Trp Tyr Phe Asp Val Trp Gly
                100                 105                 110

Thr Gly Thr Thr Val Thr Val Ser Ser
            115                 120
```

<210> SEQ ID NO 8
<211> LENGTH: 121
<212> TYPE: PRT
<213> ORGANISM: Artificial Sequence
<220> FEATURE:
<223> OTHER INFORMATION: VH for humanized antibody 161E5-VH0VL0

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Ile Asn Trp Val Arg Gln Ala Pro Gly Gln Gly Leu Glu Trp Met
        35                  40                  45

Gly Arg Ile Phe Pro Gly Ser Gly Asn Ala Tyr Tyr Asn Glu Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Ser Phe Tyr Gly Tyr Trp Tyr Phe Asp Val Trp Gly
                100                 105                 110

Gln Gly Thr Thr Val Thr Val Ser Ser
            115                 120
```

<210> SEQ ID NO 9
<211> LENGTH: 121
<212> TYPE: PRT
<213> ORGANISM: Artificial Sequence
<220> FEATURE:
<223> OTHER INFORMATION: VH for humanized antibodies 161E5-VH2VL2 and
      161E5-VH2VL3

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Ile Asn Trp Val Arg Gln Ala Pro Gly Gln Gly Leu Glu Trp Ile
        35                  40                  45
```

Ala Arg Ile Phe Pro Gly Ser Gly Asn Ala Tyr Tyr Asn Glu Lys Phe
            50                  55                  60

Lys Asp Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asp Ser Phe Tyr Gly Tyr Trp Tyr Phe Asp Val Trp Gly
            100                 105                 110

Gln Gly Thr Thr Val Thr Val Ser Ser
            115                 120

<210> SEQ ID NO 10
<211> LENGTH: 121
<212> TYPE: PRT
<213> ORGANISM: Artificial Sequence
<220> FEATURE:
<223> OTHER INFORMATION: VH for humanized antibodies 161E5-VH3VL2 and
      161E5-VH3VL3

<400> SEQUENCE: 10

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Asp Tyr
             20                  25                  30

Tyr Ile Asn Trp Val Arg Gln Arg Pro Gly Gln Gly Leu Glu Trp Ile
         35                  40                  45

Ala Arg Ile Phe Pro Gly Ser Gly Asn Ala Tyr Tyr Asn Glu Lys Phe
     50                  55                  60

Lys Asp Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Asp Ser Phe Tyr Gly Tyr Trp Tyr Phe Asp Val Trp Gly
            100                 105                 110

Gln Gly Thr Thr Val Thr Val Ser Ser
            115                 120

<210> SEQ ID NO 11
<211> LENGTH: 112
<212> TYPE: PRT
<213> ORGANISM: Artificial Sequence
<220> FEATURE:
<223> OTHER INFORMATION: VL for mouse and chimeric 161E5 antibodies

<400> SEQUENCE: 11

Asn Ile Met Met Thr Gln Ser Pro Ser Ser Leu Ala Val Ser Ala Gly
 1               5                  10                  15

Glu Lys Val Thr Met Ser Cys Lys Ser Ser Gln Ser Val Leu Tyr Ser
             20                  25                  30

Ser Asn Gln Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys His Gln
                 85                  90                  95

Tyr Leu Ser Ser Tyr Thr Phe Gly Gly Gly Thr Lys Leu Glu Ile Lys
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: VL for humanized antibody 161E5-VH0VL0

<400> SEQUENCE: 12

Glu Ile Val Met Thr Gln Ser Pro Ala Thr Leu Ser Val Ser Pro Gly
1               5                   10                  15

Glu Arg Ala Thr Leu Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys His Gln
                85                  90                  95

Tyr Leu Ser Ser Tyr Thr Phe Gly Gly Gly Thr Lys Val Glu Ile Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: VL for humanized antibodies 161E5-VH2VL2 and
      161E5-VH3VL2

<400> SEQUENCE: 13

Asn Ile Met Met Thr Gln Ser Pro Ala Thr Leu Ser Val Ser Pro Gly
1               5                   10                  15

Glu Arg Ala Thr Leu Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Asp Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys His Gln
                85                  90                  95

Tyr Leu Ser Ser Tyr Thr Phe Gly Gly Gly Thr Lys Val Glu Ile Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: VL for humanized antibodies 161E5-VH2VL3 and
      161E5-VH3VL3

<400> SEQUENCE: 14

Asn Ile Met Met Thr Gln Ser Pro Ala Thr Leu Ser Val Ser Pro Gly
1               5                   10                  15

```
Glu Arg Ala Thr Leu Ser Cys Lys Ser Ser Gln Ser Val Leu Tyr Ser
             20                  25                  30

Ser Asn Gln Lys Asn Tyr Leu Ala Trp Tyr Gln Gln Lys Pro Gly Gln
         35                  40                  45

Ser Pro Arg Leu Leu Ile Tyr Trp Ala Ser Thr Arg Glu Ser Gly Val
     50                  55                  60

Pro Asp Arg Phe Ser Gly Ser Gly Ser Gly Thr Glu Phe Thr Leu Thr
 65                  70                  75                  80

Ile Ser Ser Leu Gln Ser Glu Asp Phe Ala Val Tyr Tyr Cys His Gln
                 85                  90                  95

Tyr Leu Ser Ser Tyr Thr Phe Gly Gly Gly Thr Lys Val Glu Ile Lys
            100                 105                 110

<210> SEQ ID NO 15
<211> LENGTH: 330
<212> TYPE: PRT
<213> ORGANISM: Artificial Sequence
<220> FEATURE:
<223> OTHER INFORMATION: Human IgG1 constant region

<400> SEQUENCE: 15

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 16
<211> LENGTH: 107
<212> TYPE: PRT
<213> ORGANISM: Artificial Sequence
<220> FEATURE:
<223> OTHER INFORMATION: Human kappa constant region

<400> SEQUENCE: 16

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 17
<211> LENGTH: 936
<212> TYPE: DNA
<213> ORGANISM: Homo sapiens

<400> SEQUENCE: 17

| | | |
|---|---|---|
| atgggcgtgc ccacagccct ggaagccgga agctggaggt ggggaagcct gctgttcgcc | 60 |
| ctgttcctgg ctgcctccct gggacctgtg ccgccttca aggtggccac ccctacagc | 120 |
| ctctacgtgt gccccgaggg ccagaacgtc accctgacct gcaggctgct gggacccgtg | 180 |
| gacaagggcc acgacgtgac cttctacaag acctggtaca ggagcagcag gggcgaggtg | 240 |
| cagacctgct ccgagaggag gcccatcagg aatctgacat ccaggaccct gcacctgcat | 300 |
| cacggcggac accaggctgc caacaccagc acgacctggc tcagaggca cggactggag | 360 |
| tccgcctccg accaccatgg caacttctcc atcaccatga ggaacctgac cctgctcgac | 420 |
| agcggcctgt actgttgcct ggtggtggag atcaggcacc accacagcga gcacagagtg | 480 |
| cacggcgcca tggagctgca ggtgcagacc ggaaaggacg cccctccaa ctgcgtggtg | 540 |
| taccccagct ccagccagga gagcgagaac atcagccg ctgccctggc caccggagct | 600 |
| tgtatcgtgg gaatcctgtg cctgccctg atcctgctgc tggtctacaa gcagaggcag | 660 |
| gccgcctcca acaggagagc ccaggagctg gtcagaatgg actccaacat ccagggcatc | 720 |
| gagaaccccg gattcgaagc cagccctcct gcccagggaa tccctgaggc caaggtgagg | 780 |
| cacccccctgt cctacgtggc ccagaggcag cctagcgaga gcggcagaca cctgctgagc | 840 |

| | |
|---|---|
| gaacctagca cccctctgtc ccctcccggc cctggcgatg tgttctttcc cagcttagat | 900 |
| cctgtgcccg actcccccaa cttcgaggtc atctga | 936 |

<210> SEQ ID NO 18
<211> LENGTH: 987
<212> TYPE: DNA
<213> ORGANISM: Macaca fascicularis

<400> SEQUENCE: 18

| | |
|---|---|
| atgggcgtgc ctaccgcccc tgaggctgga tgttggaggt ggggttctct gctgttcgcc | 60 |
| ctgttcctgg ctgccagcct gggacctgtg gccgccttca aggtggctac cctgtacagc | 120 |
| ctgtacgtgt gccccgaggg ccagaatgtg acactgacct gcagagtgtt cggccccgtg | 180 |
| gacaagggcc acgacgtgac cttctataag acctggtaca ggagcagcag gggcgaggtc | 240 |
| cagacctgca gcgaaaggag gcccattagg aacctgacct tccaggacct gcatctgcac | 300 |
| catggcggcc accaagccgc caacaccagc acgacctcg ctcagaggca tggcctggag | 360 |
| agcgcctccg atcaccacgg caacttcagc atcaccatga aaacctgac cctcctggac | 420 |
| agcggactgt actgctgcct ggtggtggag atcaggcacc accacagcga gcacagagtg | 480 |
| catggcgcca tggaactcca ggtgcagacc ggcaaagacg cccctcctc ctgcgtggct | 540 |
| taccccagca gctcccagga gagcgagagc aagggcccct ccagctgccc cttttgggtg | 600 |
| atctgctccc tgctgagcag cagctgcaca cagaccctgt tcggaacact ggccctgagc | 660 |
| ccccaggctc acaggaatcc tagccccccc cctcccctgc tgctgcacat ccctagcgct | 720 |
| agctccctgg tccagagccc cgaagcccac tcccctagca tctgctccgg cgtgagcgct | 780 |
| cctctggcca gcctggagtg gctgtgcctg ggcagccatc tctggctggg caaggtgccc | 840 |
| catgacaggt actgggtgcc ccaggccgct aaatgctgcc cctcccatca gcctcccatg | 900 |
| acctccgagg gctggggcag cagaatccag ctgctgcaga tcagcgtgtt ttgcgtcagc | 960 |
| gtgttcctga ggtgttccct gctgtga | 987 |

<210> SEQ ID NO 19
<211> LENGTH: 930
<212> TYPE: DNA
<213> ORGANISM: Mus musculus

<400> SEQUENCE: 19

| | |
|---|---|
| atgggcgtcc ctgctgtgcc tgaagccagc agcccagat ggggaaccct gctgctggct | 60 |
| attttcctgg ccgctagcag gggcctggtg gccgccttca aggtgacaac acctacagc | 120 |
| ctctacgtgt gccctgaggg ccagaacgcc accctgacct gtaggattct cggccctgtg | 180 |
| tccaagggac acgacgtgac catctacaag acctggtacc tgagcagcag aggagaggtc | 240 |
| cagatgtgca aggagcacag gcccatcagg aacttcaccc tgcagcacct gcagcatcac | 300 |
| ggctccacc tgaaggccaa cgctagccac gaccagcccc agaagcatgg cctggagctg | 360 |
| gccagcgacc accacggaaa cttcagcatt accctgagga acgtgacccc cagggacagc | 420 |
| ggactgtact gctgcctggt gatcgagctg aagaaccacc accccgagca gagattctac | 480 |
| ggcagcatgg agctgcaggt gcaggccggc aaaggctccg ttctacctg tatgccagc | 540 |
| aacgagcagg acagcgacag catcacagcc gctgccctgg ccacaggagc ctgtatcgtg | 600 |
| ggaatcctgt gcctgcccct gatcctgctg ctggtgtaca gcagaggca ggtggcctcc | 660 |
| catagaagag cccaggagct ggtgaggatg gacagcagca acacccaggg cattgaaaat | 720 |

-continued

```
cccggcttcg agaccacacc cccttttccag ggcatgcccg aggccaagac aagaccccccc    780 ctgagctacg tggcccagag acagcccagc gagagcggca ggtacctgct gtccgaccct    840
agcacacccc tgagcccccc tggccctggc gacgtgttct ttcccagcct ggaccccgtg    900
cctgatagcc ccaactccga ggccatctga                                      930
```

<210> SEQ ID NO 20
<211> LENGTH: 1374
<212> TYPE: DNA
<213> ORGANISM: Artificial Sequence
<220> FEATURE:
<223> OTHER INFORMATION: Nucleotides encoding Human VSIG3-hFc fusion
      protein with a signal peptide at the N terminus

<400> SEQUENCE: 20

```
atgggctggt cctgtatcat cctgttcctg gtggctacag ccacaggcgt gcatagcctg     60
gaggtctccg agtcccctgg cagcatccaa gtcgccagag acagcctgc cgtgctgccc    120 tgtaccttca ccaccagcgc cgccctgatc aacctgaacg tcatttggat ggtgacaccc    180
ctcagcaacg ccaaccagcc cgagcaagtc attctgtacc agggcggcca gatgttcgac    240 ggagcccccca gattccacgg cagggtggga tttacaggca ccatgcccgc caccaatgtg    300
tccatcttca tcaataatac acagctgagc gacaccggca cctaccagtg tctcgtgaac    360
aacctgcccg acattggcgg caggaacatc ggcgtcaccg gcctgaccgt gctggtgcct    420
cctagcgccc ctcattgtca gatccaggga agccaggaca ttggctccga cgtgattctg    480
ctgtgctcca gcgaagaggg cattcccaga cctacctacc tgtgggagaa gctcgacaat    540
acactgaagc tgcctcccac cgccacccaa gaccaagtgc agggcacagt gaccatcagg    600
aacatctccg ccctgagctc cggactgtac cagtgtgtgg cctccaatgc catcggcacc    660
agcacctgtc tgctggacct gcaggtcatc tcccccccagc ccaggaatat cggcccttgc    720
cccgcccccg aactgctggg cggccctagc gtgttcctgt tcccccccaa gcccaaagac    780 acccctgatga tcagcagaac ccccgaggtc acctgcgtgt ggtggatgt gtcccacgaa    840 gatcctgagg tgaagttcaa ctggtacgtc gacggcgtgg aggtgcacaa cgccaagaca    900
aaacccaggg aggagcagta caactccacc tataggggtgg tcagcgtgct caccgtcctg    960
catcaggact ggctgaatgg caaggaatac aagtgtaagg tgtccaacaa ggcccctgccc   1020 gcccccatcg agaagaccat cagcaaagcc aagggccagc ctaggagcc ccaagtgtac   1080 accctgcccc ccagcaggga cgagctgacc aaaaaccagg tgagcctgac atgcctggtg   1140
aagggcttct accccagcga catcgccgtg gagtgggagt ccaacggcca gcctgagaat   1200
aactacaaga ccaccccccc tgtgctcgat tccgacggca gcttcttcct gtacagcaag   1260
ctgacagtgg acaaatccag atggcagcag ggcaacgtgt tcagctgttc cgtgatgcat   1320
gaggccctgc acaaccacta tacccagaag agcctgagcc tctcccccgg caag         1374
```

ANTIBODIES BINDING VISTA AND USES THEREOF

FIELD OF THE INVENTION

The present disclosure relates to an antibody or binding fragments thereof specifically binding to human VISTA, preparation and use thereof, especially its use in treatment of human diseases associated with VISTA, such as cancers and infectious diseases.

BACKGROUND OF THE INVENTION

As a member of B7 family, V-domain Ig suppressor of T cell activation (VISTA), also referred to as PD-1H, DD1α, c10orf54, Gi24, Dies1 and B7-H5, plays an important role in the regulation of T-cell responses (Nowak E. C. et al., (2017) *Immunol Rev.* 276(1): 66-79). It is a type I transmembrane protein whose extracellular domain bears homology to PD-L1, and expressed on hematopoietic cells, antigen-presenting cells, T cells and etc. (Lines J. L. et al., (2014) *Microenvironment and Immunology.* 74(7): 1924-32).

VISTAs, when expressed on antigen-presenting cells, bind as coinhibitory ligands to receptors on T cell surfaces to suppresse T cell responses. VISTAs were also expressed on CD4+ T cells as coinhibitory receptors (Flies D. B. et al., (2014) *J Clin Invest.* 124(5):1966-1975). CD4+ and CD8+ T cells stimulated with anti-CD3 in the presence of VISTA-Ig fusion protein proliferated less and produced reduced amounts of IFNγ and IL-2 (Lines J. L. et al., (2014) supra; Wang L. et al., (2011) *J Exp Med.* 208(3):577-592). Myeloid-derived suppressor cells (MDSC) isolated from mice infected with LP-BM5 retrovirus inhibited B cell proliferation in a VISTA dependent manner (Green K. A. et al., (2015) *J Virol.* 89(18): 9693-9698). Further, VISTA overexpression on MCA105 fibrosarcoma line, which naturally produced no such proteins, significantly increased tumor growth (Wang L. et al., (2011) supra).

VISTA is highly expressed within the tumor microenvironment (TME) on, e.g., monocytic myeloid derived suppressor cells (M-MDSCs) and regulatory T cells (Tregs), and anti-VISTA monotherapy reshaped the suppressive nature of the TME by reducing the number of MDSCs and tumor specific Tregs (Lines, J. L. et al., (2014) *Cancer Res.* 74(7):1924-1932). The monotherapy with a blocking anti-VISTA monoclonal antibody significantly reduced tumor growth in many solid tumor models, including B16/OVA melanoma, B16/BL6 melanoma, MB49 bladder carcinoma, and PTEN/BRAF inducible melanoma, regardless of the immunogenic status or origin (Mercier I. L. et al., (2014) *Cancer Res.* 74(7):1933-1944). These promising results from animal tumor studies led to phase I/II anti-VISTA monotherapy clinical trials with anti-VISTA antibodies JNJ-61610588 and JNJ-63723283 (both from Janssen) in patients with advanced solid tumors, e.g., non-small cell lung cancer (NCT02671955: A study of safety, pharmacokinetics, pharmacodynamics of JNJ-61610588 in participants with advanced cancer; Calvo E. et al., (2018) *Clinical Oncology* 36(5-suppl):58). In another ongoing clinical trial, patients with advanced tumors and lymphomas were administered with a small molecule CA-170 (Curis) antagonizing VISTA, PD-L1 and PD-L2 pathways (NCT02812875: A study of CA-170 (oral PD-L1, PD-L2 and VISTA checkpoint antagonist) in patients with advanced tumors and lymphomas). Combination therapies of anti-VISTA antibody with drugs targeting CTLA-4, PD-1 or other negative checkpoint regulators were also extensively discussed and studied (Deng J. et al., (2016) *J Immunother Cancer.* 4:86; Kondo Y. et al., (2015) *J Immunol.* 194(1_suppl): 69.32; Kondo Y. et al., (2016) *Oral Oncol.* 57: 54-60).

There remains a need for more anti-VISTA antibodies with improved pharmaceutical characteristics.

SUMMARY OF THE INVENTION

The present disclosure provides an isolated monoclonal antibody, for example, a mouse, human, chimeric or humanized monoclonal antibody, that binds to VISTA (e.g., the human VISTA, and monkey VISTA).

The antibody of the present disclosure can be used for a variety of applications, including detection of the VISTA protein, and treatment of VISTA associated diseases, such as cancers and infectious diseases.

Accordingly, in one aspect, the present disclosure pertains to an isolated monoclonal antibody (e.g., a humanized antibody), or an antigen-binding portion thereof, that binds VISTA, having a heavy chain variable region that comprises a CDR1 region, a CDR2 region and a CDR3 region, wherein the CDR1 region, the CDR2 region and the CDR3 region comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in SEQ ID NOs: 1, 2 and 3, respectively, wherein, the antibody, or antigen-binding fragment thereof, binds to VISTA.

In one aspect, an isolated monoclonal antibody, or an antigen-binding portion thereof, of the present disclosure comprises a heavy chain variable region comprising an amino acid sequence having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in any one of SEQ ID NOs: 7-10, wherein the antibody or antigen-binding fragment thereof binds to VISTA.

In one aspect, an isolated monoclonal antibody, or an antigen-binding portion thereof, of the present disclosure comprises a light chain variable region that comprises a CDR1 region, a CDR2 region and a CDR3 region, wherein the CDR1 region, the CDR2 region, and the CDR3 region comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in SEQ ID NOs: 4, 5 and 6, respectively, wherein the antibody or antigen-binding fragment thereof binds to VISTA.

In one aspect, an isolated monoclonal antibody, or an antigen-binding portion thereof, of the present disclosure comprises a light chain variable region comprising an amino acid sequence having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in any one of SEQ ID NOs: 11-14, wherein the antibody or antigen-binding fragment thereof binds to VISTA.

In one aspect, an isolated monoclonal antibody, or an antigen-binding portion thereof, of the present disclosure comprises a heavy chain variable region and a light chain variable region each comprises a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in SEQ ID NOs: 1, 2, 3, 4, 5 and 6, respectively, wherein the antibody or antigen-binding fragment thereof binds to VISTA.

In one embodiment, an isolated monoclonal antibody, or the antigen-binding portion thereof, of the present disclosure comprises a heavy chain variable region and a light chain variable region, the heavy chain variable region and the light chain variable region comprising amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in (1) SEQ ID NOs: 7 and 11, respectively; (2) SEQ ID NOs: 8 and 12, respectively; (3) SEQ ID NOs: 9 and 13, respectively; (4) SEQ ID NOs: 9 and 14, respectively; (5) SEQ ID NOs: 10 and 13, respectively; (6) SEQ ID NOs: 10 and 14, respectively, wherein the antibody or antigen-binding fragment thereof binds to VISTA.

In one embodiment, an isolated monoclonal antibody, or the antigen-binding portion thereof, of the present disclosure comprises a heavy chain and a light chain, the heavy chain comprising a heavy chain variable region and a heavy chain constant region, the light chain comprising a light chain variable region and a light chain constant region, wherein, the heavy chain constant region may be human IgG1 constant region comprising an amino acid sequence having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in SEQ ID Nos:15, and the light chain constant region may be human kappa constant region comprising an amino acid sequence having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in SEQ ID Nos:16, and the heavy chain variable region and the light chain variable region comprise amino acid sequences described above, wherein the antibody or antigen-binding fragment thereof binds to VISTA. The heavy chain constant region may be engineered to induce no antibody dependent cell mediated cytotoxicity and complement dependent cytotoxicity.

The antibody of the present disclosure in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to VISTA. The antibody of the present disclosure can be a full-length antibody, for example, of an IgG1, IgG2 or IgG4 isotype. The light chain of the present disclosure may be a kappa light chain. The antibody of the present disclosure in other embodiments may be a single chain antibody, or consists of antibody fragments, such as Fab or Fab'2 fragments.

The exemplary antibody, or antigen-binding fragment, of the present disclosure binds specifically to human and monkey VISTA with the binding affinity/activity comparable to, or better than, that of prior art antibody such as JNJ-VSTB174 (also referred to as JNJ hereinafter, JANSSEN PHARMACEUTICA). The exemplary antibody, or antigen-binding fragment, of the present disclosure binds to a different VISTA epitope as compared to JNJ-VSTB174. The antibody, or antigen-binding fragment, of the present disclosure promotes T cell activation and provides comparable, if not better, T cell activation effect and in vivo anti-tumor effect.

The present disclosure also provides exemplary bispecific molecules comprising an antibody, or antigen-binding portion thereof, of the present disclosure, linked to a second functional moiety (e.g., a second antibody) having a different binding specificity than said antibody, or antigen-binding portion thereof.

Compositions comprising an antibody, or antigen-binding portion thereof, or bispecific molecule of the present disclosure, and a pharmaceutically acceptable carrier, are also provided.

Nucleic acid molecules encoding the antibodies, or antigen-binding portions thereof, of the present disclosure are also encompassed by the present disclosure, as well as expression vectors comprising such nucleic acids and host cells comprising such expression vectors. A method for preparing an anti-VISTA antibody using the host cell comprising the expression vector is also provided, comprising steps of (i) expressing the antibody in the host cell and (ii) isolating the antibody from the host cell or its cell culture.

In another aspect, the present disclosure provides a method for enhancing an immune response in a subject, comprising administering to the subject a therapeutically effective amount of the antibody, or antigen-binding portion thereof, of the present disclosure. In some embodiments, the method comprises administering a composition, a bispecific molecule of the present disclosure.

In another aspect, the present disclosure provides a method for treating an infectious disease in a subject in need thereof, comprising administering to the subject a therapeutically effective amount of the antibody, or antigen-binding portion thereof, of the present disclosure. In some embodiments, the method comprises administering a composition, or a bispecific molecule, of the present disclosure. In some embodiments, additional agents can be administered with the antibody, or an antigen-binding portion thereof, of the present disclosure, such as antibacterial, antiviral, antifungal, and antiparasitic agents.

In yet another aspect, the present disclosure provides a method for preventing, treating or ameliorating a cancer disease in a subject, comprising administering to the subject a therapeutically effective amount of the antibody, or antigen-binding portion thereof, of the present disclosure. The cancer may be a solid or non-solid tumor, including, but not limited to, B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, and nasopharynx cancer. In some embodiments, the cancer may be selected from the group consisting of melanoma, bladder carcinoma, lung cancer, lymphomas, and colon adenocarcinoma. In some embodiments, the method comprises administering a composition, or a bispecific molecule of the present disclosure. In some embodiments, at least one additional anti-cancer antibody can be administered with the antibody, or an antigen-binding portion thereof, of the present disclosure, such as an anti-PD-1 antibody, an anti-PD-L1 antibody, an anti-LAG-3 antibody and/or an anti-CTLA-4 antibody. In yet another embodiment, an antibody, or an antigen-binding portion thereof, of the present disclosure is administered with a cytokine (e.g., IL-2 and/or IL-21), or a costimulatory antibody (e.g., an anti-CD137 and/or anti-GITR antibody). In another embodiment, an antibody, or an antigen-binding portion thereof, of the present disclosure is administered with a chemotherapeutic agent, which may be a cytotoxic agent, such as epirubicin, oxaliplatin, and/or 5-fluorouracil (5-FU). The antibodies of the present disclosure can be, for example, mouse, human, chimeric or humanized antibodies.

Other features and advantages of the instant disclosure will be apparent from the following detailed description and examples, which should not be construed as limiting. The contents of all references, Genbank entries, patents and published patent applications cited throughout this application are expressly incorporated herein by reference.

DETAILED DESCRIPTION OF THE INVENTION

Figure 1:
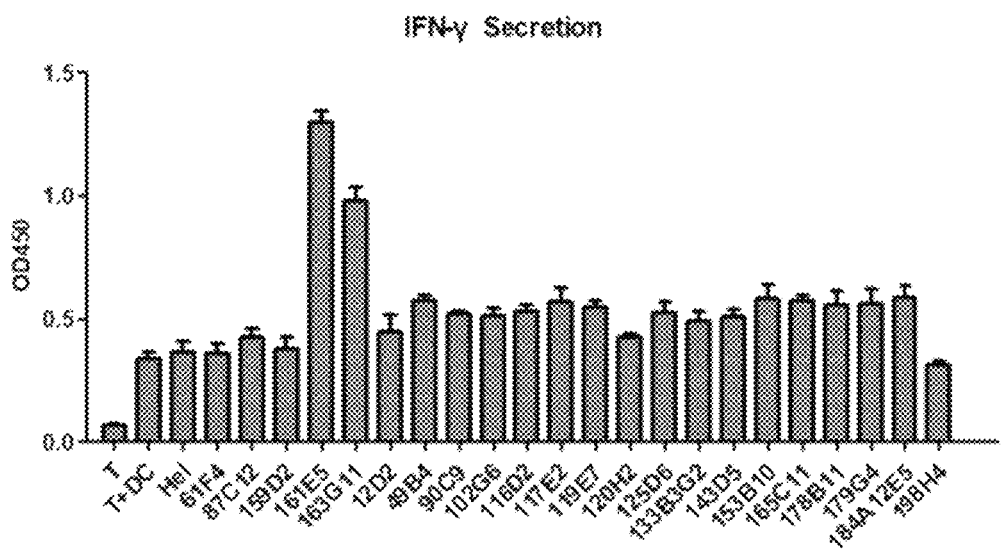
FIG. 1 shows the role of mouse anti-VISTA antibodies on APC-mediated T cell activation. Treatment of anti-VISTA 161E5 antibody at 100 μg/ml increased IFN-γ secrection by T cells (A), and treatment of anti-VISTA 161E5 antibody increased IFN-γ secrection by T cells in a dose dependent manner (B).
Figure 1:
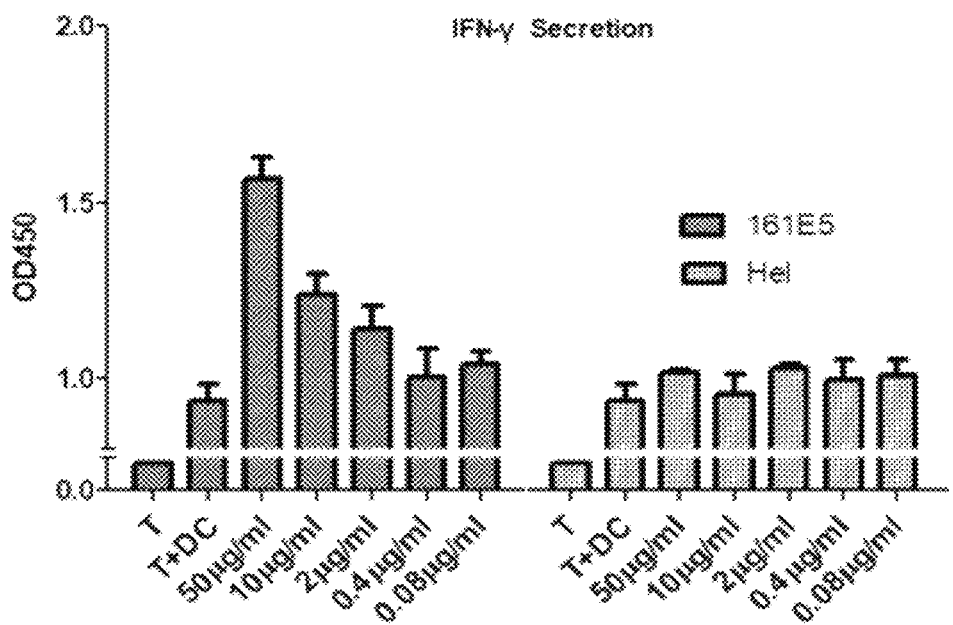

To ensure that the present disclosure may be more readily understood, certain terms are first defined. Additional definitions are set forth throughout the detailed description.

The term "VISTA" refers to V-domain Ig suppressor of T cell activation. The term "VISTA" comprises variants, isoforms, homologs, orthologs and paralogs. For example, an antibody specific for a human VISTA protein may, in certain cases, cross-react with a VISTA protein from a species other than human, such as monkey. In other embodiments, an antibody specific for a human VISTA protein may be completely specific for the human VISTA protein and exhibit no cross-reactivity to other species or of other types, or may cross-react with VISTA from certain other species but not all other species.

The term "human VISTA" refers to a VISTA protein having an amino acid sequence from a human, such as the amino acid sequence of human VISTA having a Genbank accession number of NP_071436. The terms "monkey or cyno VISTA" and "mouse VISTA" refer to monkey and mouse VISTA sequences, respectively, e.g. those with the amino acid sequences having Genbank Accession Nos. XP_015311697 and NP_001153044, respectively.

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a VISTA protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a VISTA protein is substantially free of antibodies that specifically bind antigens other than VISTA proteins). An isolated antibody that specifically binds a human VISTA protein may, however, have cross-reactivity to other antigens, such as VISTA proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the present disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimetic antibody is an antibody having genetic material from a certain species with genetic material from another species.

The term "humanized antibody", as used herein, refers to an antibody from non-human species whose protein sequences have been modified to increase similarity to antibody variants produced naturally in humans.

The phrases "an antibody recognizing an antigen" and "an antibody specific for an antigen" are used interchangeably herein with the term "an antibody which binds specifically to an antigen."

As used herein, an antibody that "specifically binds to human VISTA" is intended to refer to an antibody that binds to human VISTA protein (and possibly a VISTA protein from one or more non-human species) but does not substantially bind to non-VISTA proteins. Preferably, the antibody binds to human VISTA protein with "high affinity", namely with a $K_D$ of $5.0 \times 10^{-8}$ M or less, more preferably $1.0 \times 10^{-8}$ M or less, and more preferably $5.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-8}$ M or less, even more preferably $5.0 \times 10^{-9}$ M or less and even more preferably $1.0 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the present disclosure are described in further detail in the following subsections.

Anti-VISTA Antibodies Having Binding Specificity to Human VISTA and Advantageous Functional Properties The exemplary antibody, or antigen-binding fragment, of the present disclosure specifically binds to human VISTA with high affinity, e.g., with a $K_D$ of $7.0 \times 10^{-10}$ M or less, preferably $1.0 \times 10^{-11}$ M or less, and blocks VISTA-VSIG3 interaction. The exemplary antibodies of the present disclosure also have cross-reactivity with monkey VISTA, but do not bind to mouse VISTA.

The exemplary antibody, or antigen-binding fragment, of the present disclosure binds to a different VISTA epitope as compared to JNJ-VSTB174, and promotes T cell activation.

The exemplary antibody, or antigen-binding fragment, of the present disclosure has in vivo anti-tumor effect comparable to or better than prior art anti-VISTA antibodies, and can be used in combination with, e.g., an anti-PD-1 antibody.

Preferred antibodies of the present disclosure are monoclonal antibodies. Additionally or alternatively, the antibodies can be, for example, mouse, chimeric or humanized monoclonal antibodies.

Monoclonal Anti-VISTA Antibody

An exemplary antibody of the present disclosure is the monoclonal antibody structurally and chemically characterized as described below and in the following Examples. The $V_H$ amino acid sequence of an exemplary anti-VISTA antibody comprises or is set forth in any one of SEQ ID NOs: 7-10. The $V_L$ amino acid sequence of an exemplary anti-VISTA antibody comprises or is shown in any one of SEQ ID NOs:11-14. The amino acid sequence ID numbers of the heavy/light chain variable regions of exemplary antibodies are summarized in Table 1 below, some clones sharing the same $V_H$ or $V_L$. The heavy chain constant region for an exemplary antibodies may be human IgG1 constant region having an amino acid sequence of SEQ ID NO: 15, and the light chain constant region for an exemplary antibodies may be human kappa constant region having an amino acid sequence of SEQ ID NO: 16. The heavy chain constant region may be engineered to induce no antibody dependent cell mediated cytocoxicity and complement dependent cytotoxicity.

The heavy chain variable region CDRs and the light chain variable region CDRs in Table 1 and 7 have been defined by the Kabat numbering system. However, as is well known in the art, CDR regions can also be determined by other systems such as Chothia, IMGT, AbM, or Contact numbering system/method, based on heavy chain/light chain variable region sequences.

The $V_H$ and $V_L$ sequences (or CDR sequences) of other anti-VISTA antibodies which bind to human VISTA can be "mixed and matched" with the $V_H$ and $V_L$ sequences (or CDR sequences) of the anti-VISTA antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the present disclosure, or an antigen binding portion thereof, comprises:
(a) a heavy chain variable region comprising an amino acid sequence listed above in Table 1; and
(b) a light chain variable region comprising an amino acid sequence listed above in Table 1, or the $V_L$ of another anti-VISTA antibody, wherein the antibody specifically binds human VISTA.

In another embodiment, an antibody of the present disclosure, or an antigen binding portion thereof, comprises:
(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-VISTA antibody, wherein the antibody specifically binds human VISTA.

In yet another embodiment, the antibody, or antigen binding portion thereof, includes the heavy chain variable CDR2 region of anti-VISTA antibody combined with CDRs of other antibodies which bind human VISTA, e.g., CDR1 and/or CDR3 from the heavy chain variable region, and/or CDR1, CDR2, and/or CDR3 from the light chain variable region of a different anti-VISTA antibody.

TABLE 1

Amino acid sequence ID numbers of heavy/light chain variable regions

| mAb/<br>SEQ ID NO. | VH-<br>CDR1 | VH-<br>CDR2 | VH-<br>CDR3 | VH | VL-<br>CDR1 | VL-<br>CDR2 | VL-<br>CDR3 | VL |
|---|---|---|---|---|---|---|---|---|
| mouse and chimeric 161E5 | 1 | 2 | 3 | 7 | 4 | 5 | 6 | 11 |
| 161E5-VH0VL0 | 1 | 2 | 3 | 8 | 4 | 5 | 6 | 12 |
| 161E5-VH2VL2 | 1 | 2 | 3 | 9 | 4 | 5 | 6 | 13 |
| 161E5-VH2VL3 | 1 | 2 | 3 | 9 | 4 | 5 | 6 | 14 |
| 161E5-VH3VL2 | 1 | 2 | 3 | 10 | 4 | 5 | 6 | 13 |
| 161E5-VH3VL3 | 1 | 2 | 3 | 10 | 4 | 5 | 6 | 14 |

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the present disclosure comprise the CDR2 of the heavy chain variable region of the anti-VISTA antibody and at least the CDR3 of the heavy and/or light chain variable region of the anti-VISTA antibody, or the CDR3 of the heavy and/or light chain variable region of another anti-VISTA antibody, wherein the antibody is capable of specifically binding to human VISTA. These antibodies preferably (a) compete for binding with VISTA; (b) retain the functional characteristics; (c) bind to the same epitope; and/or (d) have a similar binding affinity as the anti-VISTA antibody of the present disclosure. In yet another embodiment, the antibodies further may comprise the CDR2 of the light chain variable region of the anti-VISTA antibody, or the CDR2 of the light chain variable region of another anti-VISTA antibody, wherein the antibody is capable of specifically binding to human VISTA. In another embodiment, the antibodies of the present disclosure may include the CDR1 of the heavy and/or light chain variable region of the anti-VISTA antibody, or the CDR1 of the heavy and/or light chain variable region of another anti-VISTA antibody, wherein the antibody is capable of specifically binding to human VISTA.

Conservative Modifications

In another embodiment, an antibody of the present disclosure comprises a heavy and/or light chain variable region sequences of CDR1, CDR2 and CDR3 sequences which differ from those of the anti-VISTA antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:
(a) the heavy chain variable region CDR1 sequence comprises a sequence listed in Table 1 above, and/or conservative modifications thereof; and/or
(b) the heavy chain variable region CDR2 sequence comprises a sequence listed in Table 1 above, and/or conservative modifications thereof; and/or
(c) the heavy chain variable region CDR3 sequence comprises a sequence listed in Table 1 above, and conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human VISTA.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the present disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Engineered and Modified Antibodies

Antibodies of the present disclosure can be prepared using an antibody having one or more of the $V_H/V_L$ sequences of the anti-VISTA antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the present disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the present disclosure provides isolated anti-VISTA monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the present disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the present disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present disclosure to thereby produce an antibody with altered glycosylation. For example, the cell lines Ms704, Ms705, and Ms709 lack the fucosyltransferase gene, FUT8 ($\alpha$(1,6)-fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application corresponding to Alston & Bird LLP 60/836,998, filed on Aug. 11, 2006. PCT Publication WO 99/54342 describes cell lines engineered to express glycoprotein-modifying glycosyl transferases (e.g., $\beta$(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180). Alternatively, the fucose residues of the antibody can be cleaved off using a fucosidase enzyme; e.g., the fucosidase $\alpha$-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the present disclosure. See, e.g., EPO 154 316 and EP 0 401 384.

Antibody's Physical Properties

Antibodies of the present disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-VISTA antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-VISTA antibody that contains a pI value that falls in the normal range. This can be achieved either by selecting antibodies with a pI in the normal range or by mutating charged surface residues.

Nucleic Acid Molecules Encoding Antibodies of the Disclosure

In another aspect, the present disclosure provides nucleic acid molecules that encode heavy and/or light chain variable regions, or CDRs, of the antibodies of the present disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the present disclosure can be, e.g., DNA or RNA and may or may not contain intronic sequences. In a preferred embodiment, the nucleic acid is a cDNA molecule.

Nucleic acids of the present disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the present disclosure include those encoding the $V_H$ and $V_L$ sequences of the VISTA monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Monoclonal Antibodies of the Disclosure

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Disclosure

Antibodies of the present disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or (3-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the present disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the present disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the present disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Bispecific Molecules

In another aspect, the present disclosure features bispecific molecules comprising one or more antibodies of the present disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-VISTA binding specificity, a third specificity for e.g., PD-1.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Pharmaceutical Compositions

In another aspect, the present disclosure provides a pharmaceutical composition comprising one or more antibodies of the present disclosure formulated together with a pharmaceutically acceptable carrier. The composition may optionally contain one or more additional pharmaceutically active ingredients, such as another antibody, such as an anti-PD-1 or anti-CTLA antibody. The pharmaceutical compositions of the present disclosure also can be administered in a combination therapy with, for example, another anti-cancer agent, or an antimicrobial agent.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the present disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-VISTA antibody of the present disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-VISTA antibody of the present disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the present disclosure can be formulated to ensure proper distribution in vivo. For example, to ensure that the therapeutic antibody of the present disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) J. Clin. Pharmacol. 29:685; Umezawa et al., (1988) Biochem. Biophys. Res. Commun. 153:1038; Bloeman et al., (1995) FEBS Lett. 357:140; M. Owais et al., (1995) Antimicrob. Agents Chemother. 39:180; Briscoe et al., (1995) Am. J. Physiol. 1233:134; Schreier et al., (1994) J. Biol. Chem. 269:9090; Keinanen and Laukkanen (1994) FEBS Lett 346:123; and Killion and Fidler (1994) Immunomethods 4:273.

Uses and Methods of the Disclosure

Antibodies (compositions and bispecifics) of the present disclosure have numerous in vitro and in vivo utilities involving, for example, treatment and/or prevention of cancers or infectious diseases. The antibodies can be administered to human subjects, e.g., in vivo, to inhibit tumor growth.

Given the ability of anti-VISTA antibodies of the present disclosure to promote T cell activation, and therefore inhibit proliferation and survival of cancer cells, the present disclosure provides methods for inhibiting growth of tumor cells in a subject comprising administering to the subject an antibody of the present disclosure. Non-limiting examples of tumors that can be treated by antibodies of the present disclosure include, but not limited to, B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, and nasopharynx cancer, original and/or metastatic. Additionally, refractory or recurrent malignancies whose growth may be inhibited using the antibodies of the present disclosure.

In another aspect, the present disclosure provides a method for treating an infectious disease in a subject, comprising administering to the subject a therapeutically effective amount of the antibody, or antigen-binding portion thereof, of the present disclosure. Additional antimicrobial agents can be administered with the antibody, or an antigen-binding portion thereof, of the present disclosure.

Generally speaking, the antibodies of the present disclosure can be used to enhance an immune response in a subject.

These and other methods of the present disclosure are discussed in further detail below.

Combination Therapy

In another aspect, the present disclosure provides methods of combination therapy in which an anti-VISTA antibody (or antigen-binding portion thereof) of the present disclosure is co-administered and/or co-formulated with one or more additional antibodies that are effective in inhibiting tumor growth or enhancing immune responses in a subject. In one embodiment, the present disclosure provides a method for inhibiting tumor growth in a subject comprising administering to the subject an anti-VISTA antibody and one or more additional antibodies, such as an anti-LAG-3 antibody, an anti-PD-L1 antibody, and anti-PD-1 antibody and/or an anti-CTLA-4 antibody. In certain embodiments, the subject is human.

The VISTA signaling blockade can also be further combined with standard cancer treatments. For example, VISTA signaling blockade can be combined with CTLA-4 and/or LAG-3 and/or PD-1 blockade and also chemotherapeutic regimes. For example, a chemotherapeutic agent can be administered with the anti-VISTA antibodies, which may be a cytotoxic agent. For example, epitubicin, oxaliplatin, and 5-FU are administered to patients receiving anti-VISTA therapy.

Optionally, the combination of anti-VISTA and one or more additional antibodies (e.g., anti-CTLA-4 and/or anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) J. Immunol. 173:4919-28). Non-limiting examples of tumor vaccines that can be used include peptides of melanoma antigens, such as peptides of gp100, MAGE antigens, Trp-2, MARTI_ and/or tyrosinase, or tumor cells transfected to express the cytokine GM-CSF.

Other therapies that may be combined with anti-VISTA antibody includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Construction of HEK293A Cell Lines Stably Expressing Human, Monkey or Mouse VISTA Cell lines stably overexpressing human, monkey or mouse VISTA were constructed using HEK293A cells (Cobioer, NJ, China). Briefly, human, monkey or mouse VISTA cDNA sequences (SEQ ID NOs:17, 18 and 19) were synthesized, and then subcloned into pLV-EGFP(2A)-Puro vectors between EcoRI and BamHI. Lentiviruses were generated in HEK-293T cells (Cobioer, NJ, China) by cotransfection of pLV-EGFP(2A)-Puro-VISTA, psPAX and pMD2.G plasmids, according to the instruction in Lipofectamine 3000 kit (Thermo Fisher Scientific, US). Three days post cotransfection, the lentiviruses were harvested from the cell culture medium (DMEM medium (Cat #: SH30022.01, Gibco) with 10% FBS (Cat #: FND500, Excell)) of respective HEK-293T cells. Finally, HEK293A cells were infected with the lentiviruses to generate HEK293A cell lines stably expressing human, monkey or mouse VISTA, namely HEK293A/humanVISTA, HEK293A/cynoVISTA or HEK293A/mouseVISTA cells. Transfected HEK293A cells were then cultured in medium (DMEM+10% FBS) containing 0.2 µg/ml puromycin (Cat #: A11138-03, Gibco) for 7 days. The expression of human VISTA and cynomolgus VISTA were confirmed by FACS using a commercially avaibale anti-VISTA antibody (PE-anti-human VISTA, Invitrogen, US, Cat #: 12-1088-42).

Similarly, the expression of mouse VISTA was confirmed by FACS using a commercially avaibale anti-mouse VISTA antibody (PE-anti-mouse VISTA, Biolegend, US, Cat #: B198378).

Example 2 Generation of Hybridoma Cell Lines Producing Exemplary Monoclonal Mouse Antibodies Against Human VISTA Murine anti-human VISTA monoclonal antibodies (mAbs) were generated using the conventional hybridoma fusion technology with some modifications.

Immunization

Thirteen BALB/c mice (Beijing Vital River Laboratory Animal Technology Co., Ltd, Beijing, China) were injected with recombinant human VISTA (ECD)-hFc (Sino Biological, CN, Cat #:13482-H02H) and/or recombinant cynomolgus VISTA (ECD)-his (Sino Biological, CN, Cat #:90801-K08H) following the scheme in Table 2 below. The human VISTA (ECD)-hFc and cynomolgus VISTA (ECD)-his were emulsified by sonication with an equal volume of Complete Freund's Adjuvant (SIGMA, USA, Cat #: F5881-10*10ML), Incomplete Freund's Adjuvant (SIGMA, USA, Cat #: F5506-6*10ML), or PBS.

ratio of 1:4. The cells were then washed 2 times and then cell fusion was performed with PEG (Sigma, Cat #: P7181). The post-fusion cells were washed with DMEM medium for three times and suspended in cell growth media (RPMI medium 1640 (Gibco, Cat #:C22400500CP)) supplemented with 10% FBS and 1×HAT (Sigma, H0262). The cell suspension was plated into 96 well cell culture plates, 200 µl per well ($5\times10^4$ cells/well), and incubated in a 37° C. humidified 5% $CO_2$ incubator for 7 days. Then, the growth media was replaced by fresh growth medium supplemented with 10% FBS+1×HT (Sigma, H0137). 2-3 days later, hybridoma cells were screened by ELISA and FACS.

Screening of Hybridoma Cell Lines by ELISA

High-throughput ELISA binding assay was firstly used to screen for hybridoma clones producing monoclonal antibodies binding to human VISTA (ECD)-his (Sino Biological, CN, Cat #:13482-H08H). The antibodies binding to human VISTA were further tested for their abilities to cross-react with cynomolgus or mouse VISTA, using cynomolgus VISTA (ECD)-his (Sino Biological, CN, Cat #: 90801-K08H) and mouse VISTA-his (Sino Biological, CN, Cat #: 511550-M08H).

With the ELISA assays, 151 hybridoma clones were identified to have specific binding to both human and monkey VISTA.

TABLE 2

| | Immunization scheme | | | | |
|---|---|---|---|---|---|
| | Primary | 1st Boost | 2nd Boost | 3rd Boost | Final Boost |
| | | | Day | | |
| | 0 | 14 | 28 | 42 | 56 |
| Protein and dose | Human VISTA (ECD)-hFc (50 µg/mouse) | Human VISTA (ECD)-hFc (50 µg/mouse) | cynomolgus VISTA (ECD)-his (50 µg/mouse) | Human VISTA (ECD)-hFc (50 µg/mouse) | cynomolgus VISTA (ECD)-his (25 µg/mouse) + Human VISTA(ECD)-hFc (25 µg/mouse) |
| Adjuvant | Complete Freund's | Incomplete Freund's | Incomplete Freund's | Incomplete Freund's | PBS |
| Way of immunization | i.p. | i.p. | i.p. | i.p. | i.v. |

One week after each boost, 50 µl of murine serum was collected from each mouse for titer determination by ELISA using the recombinant human VISTA(ECD)-his (Sino Biological, CN, Cat #:13482-H08H), cyno VISTA (ECD)-his (Sino Biological, CN, Cat #: 90801-K08H), and mouse VISTA (ECD)-his (Sino Biological, CN, Cat #: 511550-M08H). Titer determination was also done by FACS using HEK293A overexpressing human VISTA, cynomolgus VISTA or mouse VISTA as prepared in Example 1.

Based on the ELISA and FACS analysis results after the final boost, ten mice with highest serum titers were selected for hybridoma cell line generation.

Generation of Hybridoma Cell Lines

Hybridoma cell lines were generated using the conventional hybridoma fusion technology with minor modifications.

Four days after the final boost, mice were sacrificed, and spleens were collected and prepared as single cell suspensions in PBS. The splenocytes were washed for three times with DMEM medium (Hyclone, Cat #: SH30243.01B). Viable myeloma cells SP2/0 (ATCC, CRL-1581) at the log-phase were mixed with the murine splenocytes in a Screening of Hybridoma Cell Lines by FACS The 151 hybridoma clones were further screened for their binding capacities to human, cynomolgus or mouse VISTA expressed on HEK293A cells, using the HEK293A/human VISTA cells, HEK293A/cynoVISTA cells or HEK293A/mouseVISTA cells as prepared in Example 1.

Based on the FACS screening, 120 positive clones were obtained that displayed high binding capacity to both HEK293A/humanVISTA and HEK293A/cynoVISTA cells.

Subcloning of Hybridoma Clones Producing Exemplary Anti-VISTA Antibodies

The 120 hybridoma clones were subject to 2 rounds of subcloning. During the subcloning, multiple subclones (n>3) from each parent clone were selected and confirmed by ELISA and FACS assays as described above. The subclones selected through this process were defined as hybridoma cells producing monoclonal antibodies. Finally, 106 subclones (one subclone from each parent clone) having high binding capacity to both human and monkey VISTA were obtained.

Example 3 Purification of Mouse Anti-VISTA Monoclonal Antibodies

From 106 clones obtained in Example 2, 28 clones with relatively high binding affinities to human and monkey VISTAs were selected for further characterizations. Monoclonal mouse antibodies from the 28 selected clones were purified. Briefly, hybridoma cells of each subclone were grown in T175 cell culture flasks each having 100 ml of fresh serum-free medium (Gibco, US, Cat #: 12045-076) with 1% HT supplement (Gibco, Cat #: 11067-030). Cell cultures were kept for 10 days in an incubator with 5% $CO_2$ at 37° C. Cell cultures were collected, followed by centrifugation at 3500 rpm for 5 minutes and then subject to filtration using a 0.22 μm capsule to remove the cell debris. Monoclonal mouse antibodies were then purified using a pre-equilibrated Protein-A affinity column (GE, USA, Cat #: 17040501) and eluted with elution buffer (20 mM citric acid, pH3.0-pH3.5). Then, antibodies were kept in PBS buffer (pH 7.0), and their concentrations were determined using a NanoDrop instrument.

The isotype of each purified antibody was determined by using the Rapid Isotyping Kit with Kappa and Lambda-Mouse (Thermal, USA, Cat #: 26179) and Mouse Monoclonal Antibody Isotyping Reagents (Sigma, USA, Cat #: IS02-1KT), following the manufacturer's manuals.

Most clones, including 163G11, produced IgG1/kappa antibodies, while the 161E5 produced IgG2a/kappa antibody. The expression titer for clone 161E5 was 8.6 mg/L.

Example 4 Purified Mouse Anti-VISTA Monoclonal Antibodies Bound to Human and Monkey VISTA Purified mouse anti-VISTA monoclonal antibodies were firstly characterized by ELISA assay to determine their binding affinities to recombinant human, monkey or mouse VISTA proteins.

ELISA plates were coated with 500 ng/ml human VISTA (ECD)-his (Sino Biological, CN, Cat #:13482-H08H) at 4° C. overnight. The wells were blocked with 200 μl of blocking buffer (PBS containing 1% BSA, 1% goat serum, and 0.05% Tween 20) for 2 hours at room temperature, and then 100 μl of serially diluted anti-VISTA antibodies (starting from 40000 ng/ml) were added to each well and incubated for 1 hour at RT. Plates were washed for 3 times with PBST (PBS+0.05% Tween 20), added with Goat-anti-mouse IgG-HRP (Simga, US, Cat #:A9309-1 ml) diluted 5000×, and incubated for 1 hour at RT. Plates were developed with freshly prepared Ultra-TMB (BD, US, Cat #:555214) for 5 minutes at RT. Absorbance was read on a SpectraMax® i3× (Molecular Devies, US) at 450 nm.

Species-cross-reactivity of the 28 VISTA mAbs to monkey or mouse VISTA was further assessed by direct ELISA. Briefly, 500 ng/ml monkey VISTA (ECD)-his (Sino Biological, CN, Cat #: 90801-K08H) or mouse VISTA-his (Sino Biological, CN, Cat #:511550-M08H) was coated on 96-well ELISA plates followed by incubation with 100 μl of serially diluted anti-VISTA antibodies (starting from 40000 ng/ml). Goat anti-mouse IgG conjugated with HRP (Sigma, US, Cat #:A9309-1 ml) was used then. Anti-VISTA antibody JNJ-VSTB174 (referred to as JNJ) (prepared using the amino acid sequences disclosed in WO 2015/097536 A2 with human IgG1/kappa constant regions) was used as the reference.

$EC_{50}$ values for binding activity of 161E5 and the reference antibody were summarized in Table 3. The data showed that antibodies from all 28 clones bound to human and monkey VISTA, and the antibodies from one clone further cross-reacted with mouse VISTA. The mouse 161E5 antibody bound to human and monkey VISTA, and did not bind to mouse VISTA.

TABLE 3

Binding capacity of representative mouse anti-VISTA mAbs to human, monkey or mouse VISTA

| Antibodies | ELISA ($EC_{50}$:M/L) | | |
| --- | --- | --- | --- |
| | hVISTA(ECD)-his | cynoVISTA(ECD)-his | muVISTA-his |
| JNJ | 3.00E−11 | 1.10E−10 | N |
| 161E5 | 3.20E−10 | 4.50E−10 | N |

Example 5 Mouse Anti-VISTA Monoclonal Antibodies Bound to Human and Monkey VISTA Expressed on HEK293A Cells To further determine whether anti-VISTA antibodies bound to human, monkey or mouse VISTA expressed on HEK293A cells, a cell-based binding assay by FACS was performed using the HEK293A cells stably overexpressing human, monkey or mouse VISTA as generated in Example 1, respectively. Briefly, $10^5$ HEK293A cells were seeded into each well of the 96-well plates and serially diluted anti-VISTA antibodies were added to the plates. After incubated at 4° C. for 1 hour, plates were washed 3 times with PBST. Then, an APC coupled Goat Anti-Mouse IgG (BioLegend, US, Cat #:405308) diluted 500× was added to the plates. After incubation at 4° C. for 1 hour, the plates were washed with PBS for 3 times and then cell fluorescence was monitored using a FACS machine (BD).

$EC_{50}$ values of 161E5 and the reference antibody were summarized in Table 4 below. The data indicated that all of the mouse anti-VISTA monoclonal antibodies showed high binding capacity to both human and monkey VISTA but did not bind to mouse VISTA.

TABLE 4

Binding affinity of mouse anti-VISTA antibodies to human, monkey and mouse VISTA

| Antibodies | FACS($EC_{50}$:M/L) | | |
| --- | --- | --- | --- |
| | HEK-293A/ hVISTA | HEK-293A/ cynoVISTA | HEK-293A/ muVISTA |
| JNJ | 2.48E−10 | 4.38E−10 | N |
| 161E5 | 6.00E−10 | 1.20E−09 | N |

Example 6 Epitope Binning

For epitope binning, a competition ELISA assay was performed. Briefly, 96-well plates were coated with 5 μg/ml JNJ antibody at 4° C. overnight. The wells were blocked with 200 μl of blocking buffer (PBS containing 1% BSA, 1% goat serum, and 0.05% Tween 20) for 2 hours at room temperature. Human VISTA (ECD)-his (Sino Biological, CN, Cat #:13482-H08H) was diluted to 0.5 μg/mL and added to the plate which was then incubated for 1 hour at RT. The ELISA plates were washed for 3 times with PBST, and then the purified antibodies were diluted to 1 μg/mL and added to each well and allowed to incubate for 1 hour at RT.

The ELISA plates were washed for 3 times with PBST, and then anti-mouse Fc-HRP (Sigma, US, Cat #: A9309-1MC) diluted at 1:20000 was added to each well and incubated for 1 hour at RT. Plates were developed with freshly prepared Ultra-TMB (Huzhou Yingchuang, CN, Cat #: TMB-S-003) for 5 minutes at RT and the absorbance was measured on SpectraMax microplate reader (Molecular Devices; US; SpectraMaxR i3X) at 450 nm (OD450).

Fourteen mouse antibodies competed with reference antibody, indicating that these antibodies and JNJ bound to the same or similar epitopes. The remaining antibodies, including those from clone 161E5, did not show competition with the reference antibody, indicating that these antibodies bound to different epitops as compared to JNJ.

Example 7 Mouse Anti-VISTA Antibodies Inhibited Human VISTA-VSIG3 Interaction

VSIG3 was reported as a ligand for VISTA (Wang, J. et al., (2019) *Immunology.* 156(1):74-85). The DNA sequence (SEQ ID NO:20) encoding the human VSIG3-hFc fusion protein linked with a signal peptide at the N terminus and a hFc-tag at the C terminus was synthesized and subcloned into XhoI/BamHI restriction sites of pCDNA3.1 (Invitrogen, Carlsbad, USA), which plasmids were transfected into HEK-293F cells (Cobioer, NJ, China). In specific, HEK-293F cells were cultured in Free Style™ 293 Expression Medium (Gibco, Cat #: 12338-018) and transfected with the plasmids using polyethyleneinimine (PEI) at a DNA: PEI ratio of 1:3, 1.5 μg DNAs per millimeter of cell medium. Transfected HEK-293F cells were cultured in an incubator at 37° C. under 5% $CO_2$ with shaking at 120 RPM. After 10-12 days, supernatants were harvested and the fusion proteins were purified as described in Example 3.

A cell-based blocking assay by FACS was performed using the HEK293A cells stably overexpressing human VISTA as generated in Example 1. Briefly, $10^5$ HEK293A/human VISTA cells were seeded into each well of the 96-well plates and serially diluted anti-VISTA antibodies were added to the plates. After incubated at 4° C. for 1 hour, plates were washed 3 times with PBST. Then 200 μg/ml VSIG3-hFc fusion proteins were added into the plate. After incubation at 4° C. for 1 hour, the plates were washed with PBS for 3 times and then an PE coupled Goat Anti-human IgG (Thermofisher, USA, Cat # PAI-86078) diluted 500× was added to the plates. After incubation at 4° C. for 1 hour, the plates were washed with PBS for 3 times and then cell fluorescence was monitored using a FACS machine (BD).

The data showed that only one antibody was not capable of blocking VISTA-VSIG3 interaction. $EC_{50}$ values of 161E5 and the reference antibody were summarized in Table 5.

TABLE 5

Blocking capacity of mouse anti-VISTA antibodies on VISTA-VSIG3 interaction

| Antibodies | VISG-3 Blocking assay $EC_{50}$(M/L) |
| --- | --- |
| JNJ | 3.92E−09 |
| 161E5 | 1.90E−08 |

Example 8 Mouse Anti-VISTA Antibodies Promoted T Cell Activation

The role of mouse anti-VISTA antibodies on T cell activation was studied by a mixed lymphocyte reaction (MLR) assay.

Briefly, PBMCs from one healthy human donor's blood sample were collected by density gradient centrifugation and then resuspended in RPMI1640 medium. PBMCs were cultured in a 37° C. incubator for 2 hours, and cells adhered to container walls were collected as isolated monocytes. The monocytes were cultured with 100 ng/ml of recombinant human GM-CSF (R&D, US, Cat #: 7954-GM) and 100 ng/ml of recombinant human IL-4 (R&D, US, Cat #: 6507-IL) in RPMI1640 mediumsupplemented with 10% FBS in a 24-well plate. Three days later, half of the medium was replaced with fresh medium. On day 6 of culturing, the culture medium was replaced by fresh medium containing 100 ng/ml of recombinant human GM-CSF (R&D, US, Cat #: 7954-GM), 100 ng/ml of recombinant human IL-4 (R&D, US, Cat #: 6507-IL), 10 ng/ml of rhTNF-α (R&D, US, Cat #: 210-TA-100), 1000 U/ml of rhIL-6 (R&D, US, Cat #7270-IL-025), 1 μg/ml PGE2 (TOCRIS, US, Cat #363-24-6) and 10 ng/ml of IL-1(3 (R&D, US, Cat #210-LB-025). The cells were cultured for another 2 days. Then, PBMCs from another healthy human donor's blood sample were collected by density gradient centrifugation and then resuspended in RPMI1640 medium. CD4+ T cells were isolated from the PBMCs using Invitrogen Dynabeads Untouched Human CD4+ T cells isolation kit (Thermal Fisher Scientific, USA, Cat #: 11346D) according to the manufacturer's instructions. The DC cells from the first donor were seeded at $2.5 \times 10^4$ cells/well and the CD4+ T cells from the second donor were seeded at $5 \times 10^4$ cells/well in a 96 well U-bottom plate. Anti-VISTA antibodies (0.08 μg/ml to 100 μg/ml), or the control antibody Hel (LifeTein, US, Cat #: LT12031) were added to the cells, and the plate was further cultured for 72 h. IFN-γ concentration was determined by ELISA (R&D, US, Cat #: SIF50) using manufacturer's protocol. The assay was done in triplicate.

As shown in Panel A of FIG. 1, highest IFN-γ levels were detected in wells treated with mouse anti-VISTA antibodies from clone 161E5. And the 161E5 antibody increased IFN-γ secretion by T cells as compared to anti-Hel isotype control, in a dose dependent manner (see Panel B, FIG. 1).

Example 9 Expression and Purification of Chimeric 161E5 Antibody

Antibody 161E5 was selected for further tests. The heavy/light chain variable region sequences of the selected candidate antibody was cloned from hybridoma cells using the standard PCR method with a set of degenerated primers as describes in literatures (Juste et al., (2006), *Anal Biochem.* 1; 349(1):159-61) and sequenced. The sequences were summarized in Table 1 and Table 7. Expression vectors were constructed by inserting the sequence encoding the heavy chain variable region plus human IgG1constant region or the sequence encoding the light chain variable region plus human kappa constant region (amino acid sequences of heavy chain constant region and light chain constant region set forth in SEQ ID NOs: 15 and 16, respectively) into XhoI/BamHI restriction sites of pCDNA3.1 (Invitrogen, Carlsbad, USA), wherein the C-terminus of the heavy chain variable region was linked to the N-terminus of the human IgG1 constant region, and the C-terminus of the light chain variable region was linked to the N-terminus of the human kappa constant region.

The expression vectors were PEI transfected into HEK-293F cells (Cobioer, NJ, China). In specific, HEK-293F cells were cultured in Free Style™ 293 Expression Medium (Gibco, Cat #: 12338-018) and transfected with the expression vectors using polyethyleneinimine (PEI) at a DNA:PEI ratio of 1:3, 1.5 µg of DNAs per millimeter of cell medium. Transfected HEK-293F cells were cultured in an incubator at 37° C. under 5% $CO_2$ with shaking at 120 RPM. After 10-12 days, supernatants were harvested and monoclonal antibodies were purified as described in Example 3.

Example 10 Chimeric 161E5 Monoclonal Antibody Bound to Human and Monkey VISTA

The chimeric 161E5 antibody was further characterized for the ability of binding to human VISTA, monkey VISTA and mouse VISTA according to the protocol of Example 4. The antibody was also tested for the ability of binding to HEK293A/humanVISTA cells, HEK293A/cynomolgus VISTA cells and HEK293A/mouseVISTA cells as generated in Example 1, according to the protocol of Example 5. The test results were shown in FIG. 2 and FIG. 3, respectively.

Figure 2:
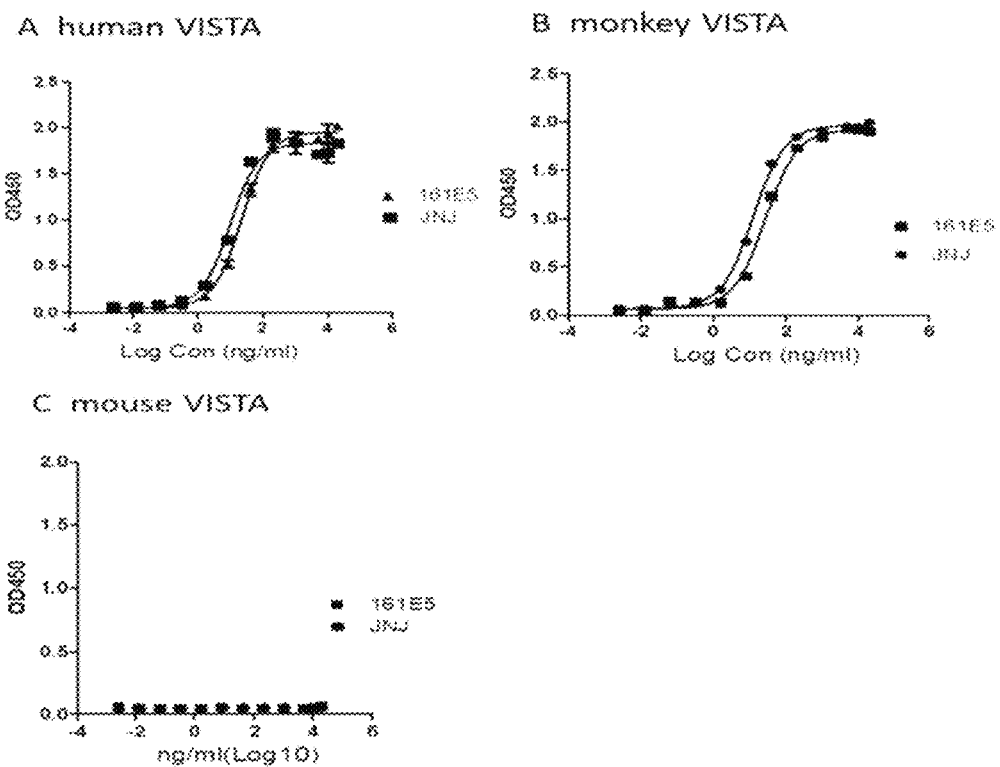
FIG. 2 shows the binding activity of mouse 161E5 anti-VISTA antibody to human VISTA (A), monkey VISTA (B) and mouse VISTA (C).
Figure 3:
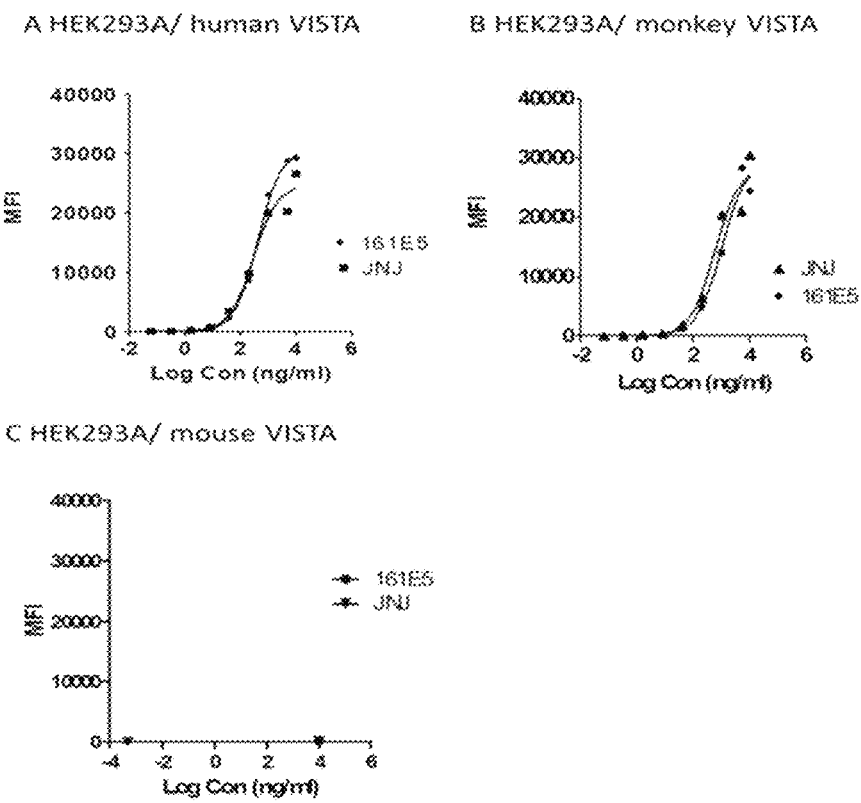
FIG. 3 shows the binding activity of mouse 161E5 anti-VISTA antibody to HEK293A/human VISTA (A), HEK293A/monkey VISTA (B), and HEK293A/mouse VISTA (C).

As shown in FIG. 2, the chimeric 161E5 antibody had high binding capacity to both human VISTA (Panel A) and monkey VISTA (Panel B), but did not bind to mouse VISTA (Panel C). Similar binding results were shown in FIG. 3.

Example 11 Humanization of Exemplary Anti-VISTA 161E5 Antibody

Based on the characterizations and assays described above, 161E5 was selected for humanization and further investigations. Humanization of the murine 161E5 antibody was conducted using the well-established CDR-grafting method (U.S. Pat. No. 5,225,539, incorporated herein by reference in its entirety) as described in detail below.

To select acceptor frameworks for humanization of murine antibody 161E5, the light and heavy chain variable region sequences of 161E5 were blasted against the human immunoglobulin gene database in NCBI website (http://www.ncbi.nlm.nih.gov/igblast/). The human germline IGVH and IGVK with the highest homology to 161E5 were selected as the acceptor for humanization. For 161E5, the human heavy chain acceptor selected was IGHV1-46*01, and the human light chain acceptor selected was IGKV4-1*01.

The three dimensional structure was simulated for variable domains of 161E5 in order to identify key framework residues that might be playing important roles in supporting CDR loop structures, thus designing back mutations in humanized antibodies.

Based on the structural modeling as described above, 9 potential back-mutations (M48I, G49A, V68A, M70L, R72V, T74K, V79A, A40R, Y95F) were identified for heavy chain of 161E5 and 5 back-mutations (E1N, V3M, I64V, A66D, A49S) were identified for light chain.

Three humanized heavy chain variable regions and three humanized light chain variable regions were designed for 161E5, with a total of 5 humanized antibodies. The sequences of the obtained humanized antibodies were summarized in Table 1 and Table 7.

The sequences encoding the heavy chain variable region plus human IgG1 constant region, and the sequence encoding light chain variable regions plus human kappa constant region (amino acid sequences of heavy chain constant region and light chain constant region set forth in SEQ ID NOs: 15 and 16, respectively) were chemically synthesized and then subcloned into GS expression vector (Invitrogen, USA) using the EcoR I/Xho I and Cla I/Hind III restriction sites respectively, wherein the C-terminus of the heavy chain variable region was linked to the N-terminus of the human IgG1 constant region, and the C-terminus of the light chain variable region was linked to the N-terminus of the human kappa constant region. All expression constructs were confirmed by DNA sequencing. The EXPiCHO expression systems (Invitrogen, USA) were transfected with heavy chain and light chain expressing vectors and transiently expressed 5 humanized anti-VISTA antibodies, following the protocol described in Example 9. The humanized antibodies were purified as described in Example 3.

Example 12 Characterization of Exemplary Chimeric and Humanized Anti-VISTA 161E5 Antibodies The chimeric and humanized anti-VISTA 161E5 antibodies were characterized for their abilities of binding to human VISTA, Monkey VISTA and mouse VISTA by ELISA according to the protocols of Example 4, and to HEK293A/human VISTA cells and HEK293A/rhesus VISTA cells, following the protocols described in Example 5.

They were also tested in SPR assays for their binding affinities to human and monkey VISTA with the BIAcore™ 8K instrument (GE Life Sciences). Briefly, 100-200 response units (RU) of human VISTA (ECD)-his protein (Sino Biological, CN, Cat #:13482-H08H) or monkey VISTA (ECD)-his protein (Sino Biological, CN, Cat #:90801-K08H) were coupled to CM5 biosensor chips (Cat #: BR-1005-30, GE Life Sciences), followed by blocking of un-reacted groups with 1M ethanolamine. Serially diluted antibodies at concentrations ranging from 0.3 µM to 10 µM were injected into the SPR running buffer (HBS-EP buffer, pH7.4, GE Life Sciences; US; Cat #:BR-1006-69) at 30 µL/minute. The binding capacitities were calculated with the RUs of blank controls subtracted. The association rate ($k_a$) and dissociation rate ($k_d$) were calculated using the one-to-one Langmuir binding model (BIA Evaluation Software, GE Life Sciences). The equilibrium dissociation constant $K_D$ was calculated as the $k_d/k_a$ ratio.

These antibodies were further tested for their abilities to stimulate T cell response by a MLR assay according to the protocol of Example 8. In addition to IFN-γ, TNFα level concentration was determined by ELISA (R&D, US, Cat #: STA00C) following the manufacturer's protocol.

Figure 4:
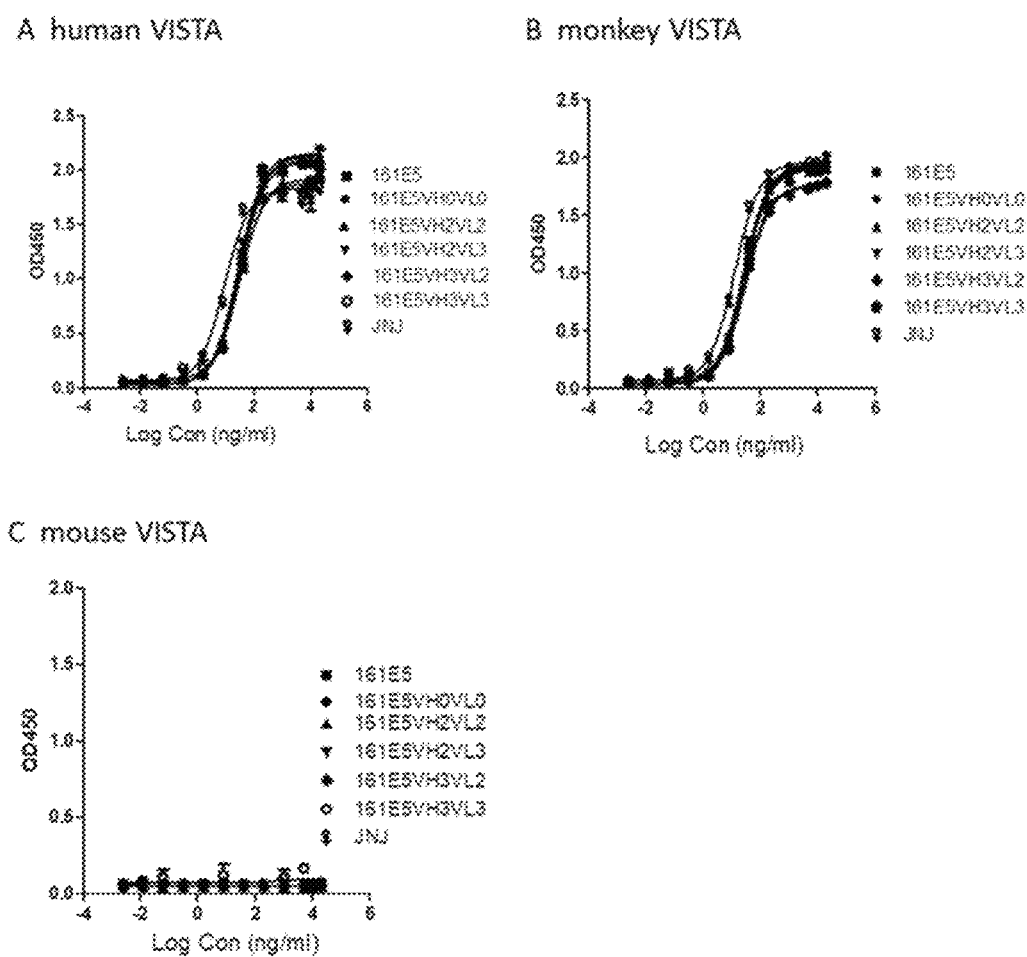
FIG. 4 shows the binding activities of chimeric and humanized 161E5 antibodies to human VISTA (A), monkey VISTA (B), and mouse VISTA (C).
Figure 5:
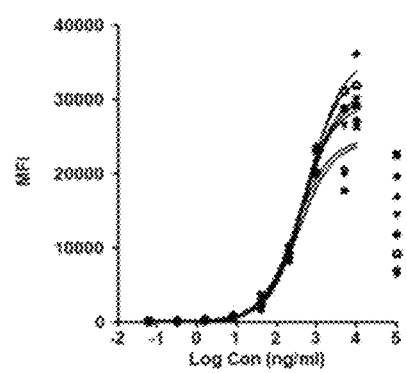
FIG. 5 shows the binding activities of chimeric and humanized 161E5 antibodies to HEK293A/human VISTA (A), HEK293A/monkey VISTA (B), and HEK293A/mouse VISTA (C).
Figure 5:
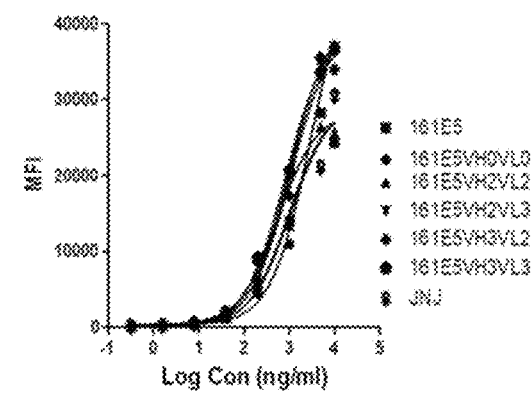
Figure 5:
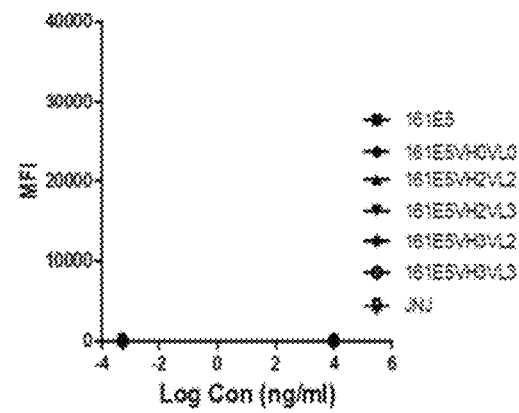

As shown in FIG. 4 and FIG. 5, the humanized anti-VISTA 161E5 antibodies had similar binding affinities to their corresponding chimeric antibody.

The binding affinities of those chimeric or humanized antibodies as measured by BIAcore™ were listed in Table 6. The chimeric and humanized 161E5 antibodies had comparable or better binding affinity to human VISTA as compared to JNJ, with the humanized antibody 161E5VH2VL3 showing the highest binding affinity.

TABLE 6

Binding affinities of anti-VISTA antibodies to human/monkey VISTA

| Antibody | Human VISTA | | | Monkey VISTA | | |
|---|---|---|---|---|---|---|
| | $K_a$ | $K_d$ | $K_D$ | $K_a$ | $K_d$ | $K_D$ |
| Chimeric 161E5 | 1.30E+5 | 1.81E−6 | 1.39E−11 | / | / | / |
| 161E5-VH2VL3 | 1.19E+5 | 2.81E−7 | 2.36E−12 | 8.79E+5 | 1.28E−5 | 1.45E−11 |
| 161E5-VH3VL3 | 1.26E+5 | 2.85E−6 | 2.26E−11 | 4.51E+5 | 1.80E−5 | 3.99E−11 |
| JNJ | 1.46E+5 | 2.27E−6 | 1.55E−11 | / | / | / |

Figure 6:
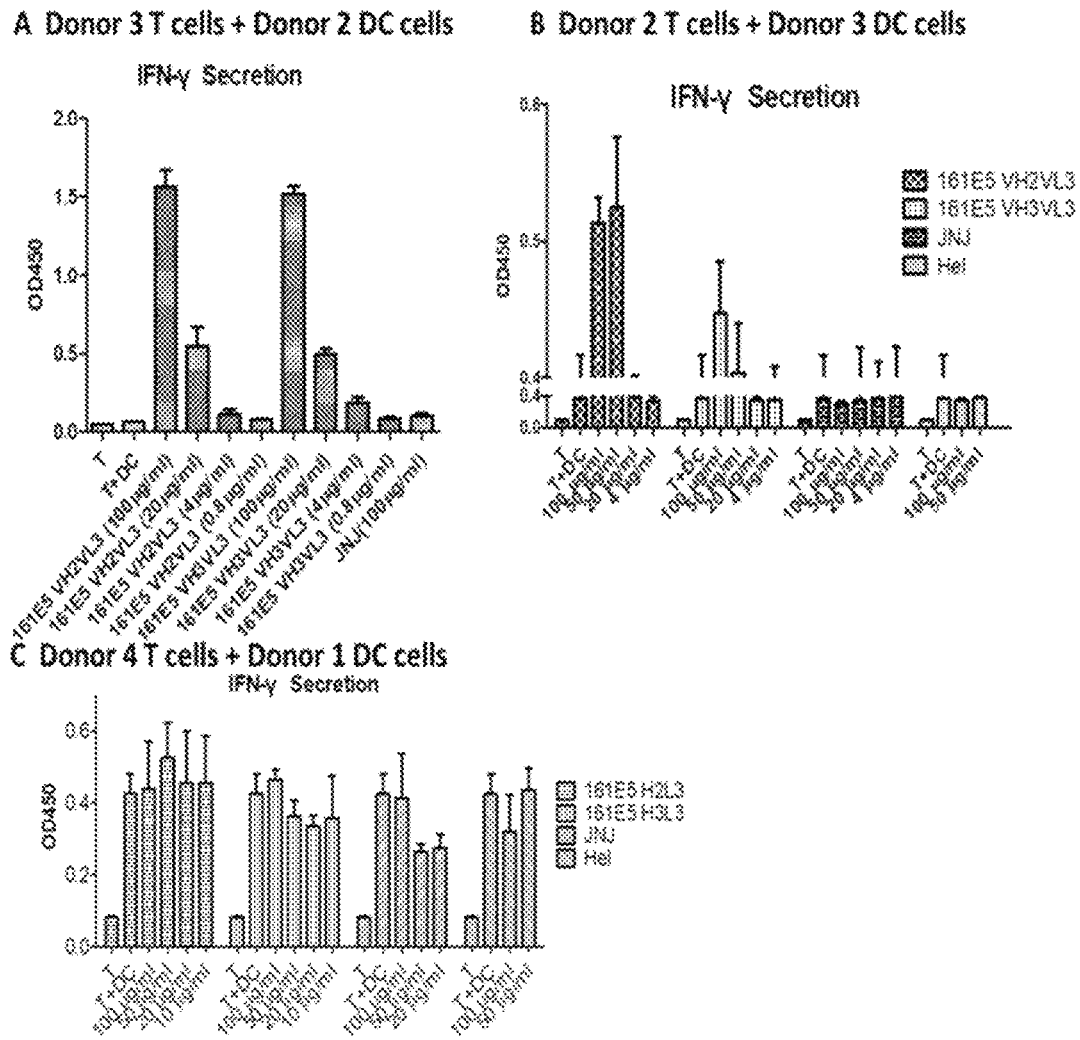
FIG. 6 shows humanized 161E5 antibodies induced IFN-γ secretion by T cells in a dose dependent manner, with T cells from donor 3 and dendritic cells from donor 2 (A), T cells from donor 2 and dendritic cells from donor 3 (B), and T cell from donor 4 and dendritic cells from donor 1 (C).

Further, as shown in FIG. 6, all humanized 161E5 antibodies promoted T cell activation, with IFN-γ levels similar to or higher than those induced by JNJ in certain donors. Antibody 161E5VH2VL3 had the strongest promotion effect on T cell response.

Example 13 Demonstration of Efficacy: Humanized Anti-VISTA 161E5 Antibodies had In Vivo Anti-Tumor Effect In vivo anti-tumor activities of anti-VISTA antibodies 161E5VH2VL3 and 161E5VH3VL3 having human IgG1/kappa constant regions were studied in an animal model established by grafting MC38 murine colon adenocarcinoma in transgenic mice with human VISTA (GemPharmatech Co. Ltd, China). Mice were subcutaneously injected with $1 \times 10^6$ MC38 cells at one flank and randomly assigned into six groups, 8 mice per group, on Day 0. These animals were then i.p. administered with 161E5VH2VL3 (10 mg/kg), 161E5VH3VL3 (10 mg/kg), anti-mouse PD-1 antibody (InVivoMAb anti-mouse PD-1(CD279), Cat # BE0146, USA) (2.5 mg/kg), 161E5VH2VL3+anti-PD-1 (10 mg/kg+2.5 mg/kg), 161E5VH3VL3+anti-PD-1 (10 mg/kg+2.5 mg/kg), or PBS at Day 0, 4, 7, 11, 14, and 18.

Tumor size and mice body weight were measured over time. Tumor measurements (width and length) were taken by caliper and tumor volume calculated by the formula TV=(length×width$^2$)/2. The experiment was terminated before the tumor volume in antibody administration groups reached 3.5 cm$^3$. One-way ANOVA was used to identify tumor volume differences.

At Day 21, the mice were sacrificed. The tumors were isolated for weighting and photographing, and then fixed in 4% paraformaldehyde buffer (Beyotime, China, Cat #: P0098), embedded in paraffin and cut into 0.5 μm-thick sections. The sections were de-paraffinized with xylene and ethanol. Then, the sections were boiled in 10 mM citric acid supplemented with 0.05% Tween-20 (pH 6.0) at 120° C. for 10 min for antigen retrieval. The sections were subsequently quenched by 2% $H_2O_2$, blocked with 10% goat serum (Haoranbio, Cat # C0005, China) and incubated overnight at 4° C. with 0.5 μg/ml monoclonal mouse anti-CD3 antibody (Cell Signaling Technology, US, CAT #99940), anti-CD4 antibody (Cell Signaling Technology, US, CAT #25229), and anti-CD8 antibody (Cell Signaling Technology, US, CAT #98941), respectively. Antibody binding was visualized with horseradish-peroxidase-labeled secondary antibodies using the polymer-based power vision antibody (Power Vision HRP goat-a-mouse, Immunologic, Duiven, the Netherlands) and a substrate-chromogen solution (Solarbio, CAT #: DA1015, China). Sections were subsequently counter-stained with Mayer's haematoxylin (Carl Roth GmbH, Karlsruhe, Germany) and subjected to evaluation by the raters.

Figure 7:
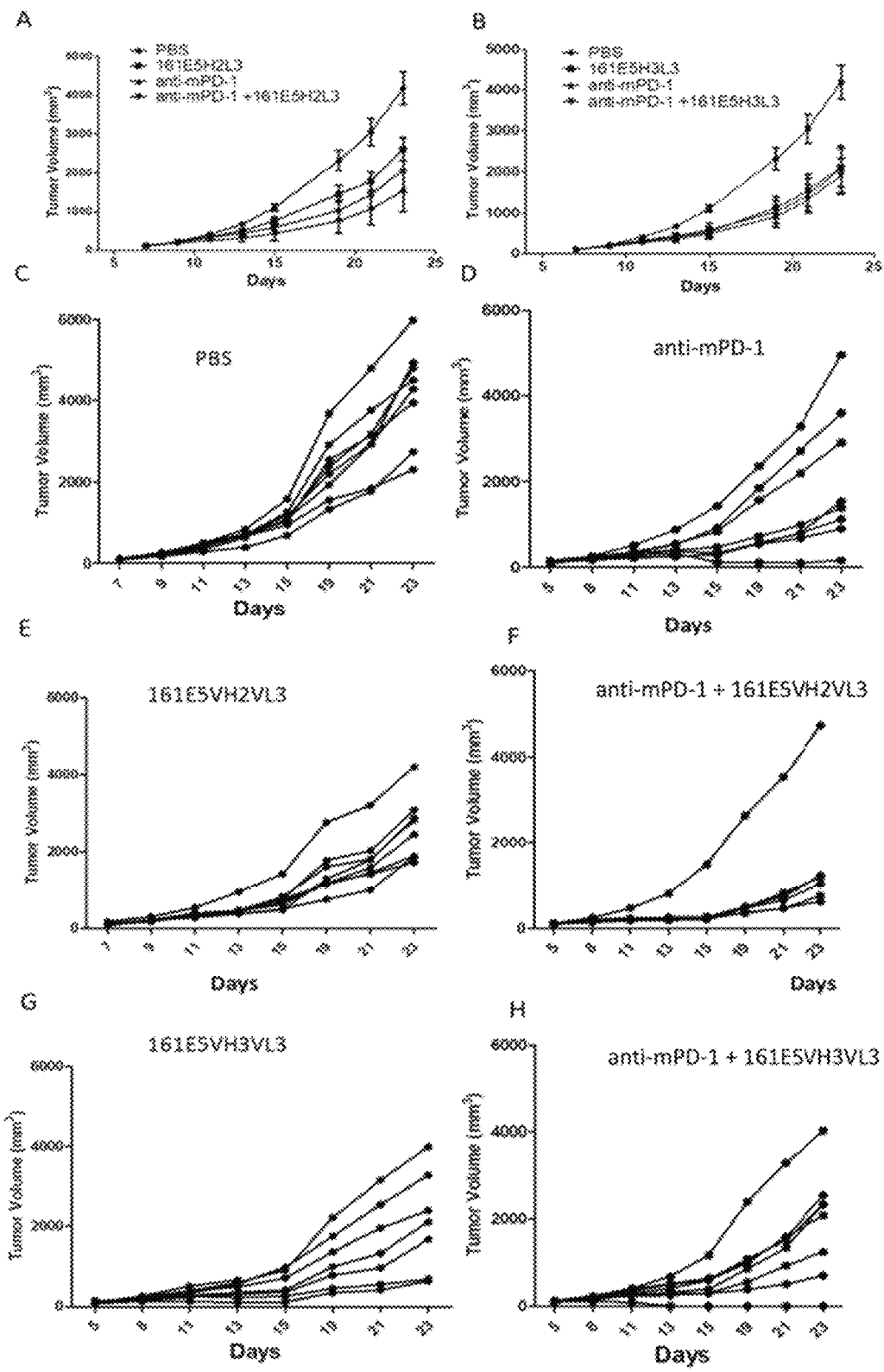
FIG. 7 shows average mice tumor volumes in groups treated with vehicle, humanized antibody 161E5VH2VL3, an anti-mPD-1 antibody, or 161E5VH2VL3 plus the anti-mPD-1 antibody (A), and in groups treated with vehicle, humanized antibody 161E5VH3VL3, an anti-mPD-1 antibody, or 161E5VH3VL3 plus the anti-mPD-1 antibody (B). Individuals responded differently to vehicle (C), the anti-mPD-1 antibody (D), 161E5VH2VL3 (E), 161E5VH2VL3 combined with the anti-mPD-1 antibody (F), 161E5VH3VL3 (G) or 161E5VH2VL3 combined with the anti-mPD-1 antibody (H).
Figure 8:
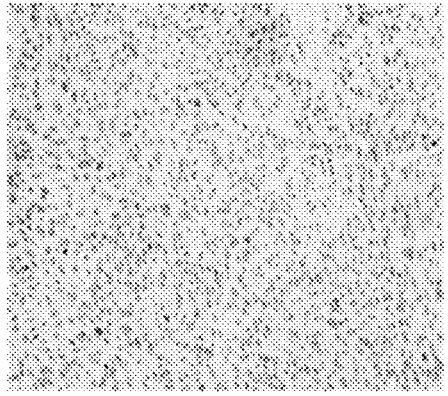
FIG. 8 shows CD3 (A), CD8 (B) and CD4 (C) stainings in tumor sections from mice treated with vehicle, and CD3 (D), CD8 (E) and CD4 (F) stainings in tumor sections from mice treated with humanized antibody 161E5VH2VL3.
Figure 8:
Figure 8:
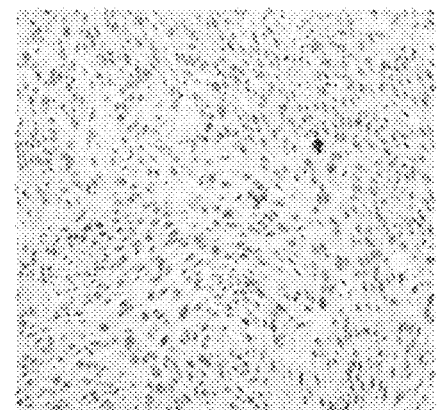
Figure 8:
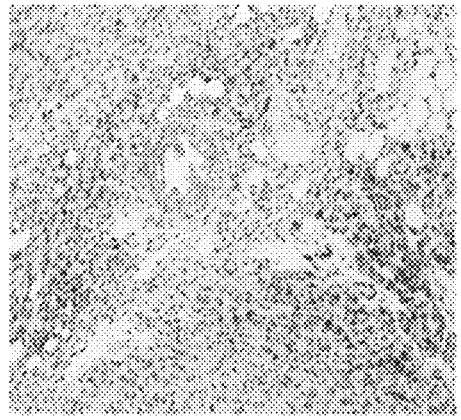
Figure 8:
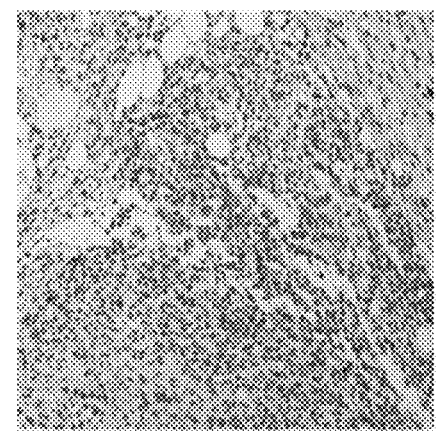
Figure 8:
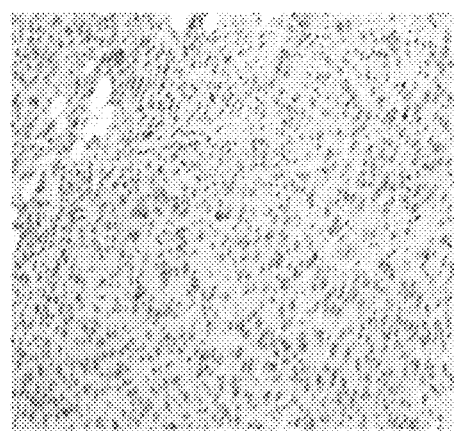

As shown in FIG. 7, the treatment with antibody 161E5VH2VL3 or 161E5VH3VL3 significantly reduced mice tumor volume, as compared to vehicle administration, although individuals responded differently. When the anti PD-1-antibody was used in combination with 161E5VH2VL3, the anti-tumor effect was even a bit better compared to single antibody administration. Results in FIG. 8 indicated that treatment of antibody 161E5VH2VL3 evidently increased CD3$^+$ and CD8$^+$ cells, as compared to vehicle control group.

The sequences in the application are summarized as follows in Table 7.

TABLE 7

Sequences

Description/Sequence/SEQ ID NO.

VH-CDR1 for mouse, chimeric and humanized 161E5 antibodies (SEQ ID NO: 1)
DYYIN

VH-CDR2 for mouse, chimeric and humanized 161E5 antibodies (SEQ ID NO: 2)
RIFPGSGNAYYNEKFKD VH-CDR3 for mouse, chimeric and humanized 161E5 antibodies (SEQ ID NO: 3)
DDSFYGYWYFDV VL-CDR1 for mouse, chimeric and humanized 161E5 antibodies (SEQ ID NO: 4)
KSSQSVLYSSNQKNYLA VL-CDR2 for mouse, chimeric and humanized 161E5 antibodies (SEQ ID NO: 5)
WASTRES VL-CDR3 for mouse, chimeric and humanized 161E5 antibodies (SEQ ID NO: 6)
HQYLSSYT VH for mouse and chimeric 161E5 antibodies (SEQ ID NO: 7)
QVQLKQSGAELVRPGASVKLSCKASGYSFTDYYINWVKQRPGQGLEWIARIFPGSGNAYYNEKFKDK
ATLTVEKSSSAAYMQLSSLTSEDSAVYFCARDDSFYGYWYFDVWGTGTTVTVSS VH for humanized antibody 161E5-VH0VL0 (SEQ ID NO: 8)

TABLE 7-continued

Sequences

Description/Sequence/SEQ ID NO.

QVQLVQSGAEVKKPGASVKVSCKASGYSFTDYYINWVRQAPGQGLEWMGRIFPGSONAYYNEKFK
DRVTMTRDTSTSTVYMELSSLRSEDTAVYYCARDDSFYGYWYFDVWGQGTTVTVSS

VH for humanized antibodies
161E5-VH2VL2 and 161E5-VH2VL3                                      (SEQ ID NO: 9)
QVQLVQSGAEVKKPGASVKVSCKASGYSFTDYYINWVRQAPGQGLEWIARIFPGSGNAYYNEKFKD
RATLTVDKSTSTAYMELSSLRSEDTAVYYCARDDSFYGYWYFDVWGQGTTVTVSS VH for humanized antibodies
161E5-VH3VL2 and 161E5-VH3VL3                                     (SEQ ID NO: 10)
QVQLVQSGAEVKKPGASVKVSCKASGYSFTDYYINWVRQRPGQGLEWIARIPPGSGNAYYNEKFKD
RATLTVDKSTSTAYMELSSLRSEDTAVYFCARDDSFYGYWYFDVWGQGTTVTVSS VL for mouse and chimeric
161E5 antibodies                                                  (SEQ ID NO: 11)
NIMMTQSPSSLAVSAGEKVTMSCKSSQSVLYSSNQKNYLAQYQQKPGQSPKLLIYWASTRESGVPDR
FTGSGSGTDFTLTISSVQAEDLAVYYCHQYLSSYTFGGGTKLEIK VL for humanized antibody
161E5-VH0VL0                                                      (SEQ ID NO: 12)
EIVMTQSPATLSVSPGERATLSCKSSQSVLYSSNQKNYLAWYQQKPGQAPRLLIYWASTRESGIPARFS
GSGSGTEFTLTISSLQSEDFAVYYCHQYLSSYTFGGGTKVEIK VL for humanized antibodies
161E5-VH2VL2 and 161E5-VH3VL2                                     (SEQ ID NO: 13)
NIMMTQSPATLSVSPGERATLSCKSSQSVLYSSNQKNYLAWYQQKPGQAPRLLIYWASTRESGVPDR
FSGSGSGTEFTLTISSLQSEDFAVYYCHQYLSSYTFGGGTKVEIK VL for humanized antibodies
161E5-VH2VL3 and 161E5-VH3VL3                                     (SEQ ID NO: 14)
NIMMTQSPATLSVSPGERATLSCKSSQSVLYSSNQKNYLAWYQQKPGQSPRLLIYWASTRESGVPDRF
SGSGSGTEFTLTISSLQSEDFAVYYCHQYLSSYTFGGGTKVEIK Human IgG1 constant region                                        (SEQ ID NO: 15)
ASTKGPSVFPLAPSSKSTSGGTAALGCLVKDYFPEPVTVSWNSGALTSGVHTFPAVLQSSGLYSLSSV
VTVPSSSLGTQTYICNVNIAKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYN STYRVVSVLTVLHQDWLNGKEY
KCKVSNKALPAPIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSLSPGK Human kappa constant region                                       (SEQ ID NO: 16)
RTVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC Human VISTA                                                       (SEQ ID NO: 17)
ATGGGCGTGCCCACAGCCCTGGAAGCCGGAAGCTGGAGGTGGGGAAGCCTGCTGTTCGCCCTGT
TCCTGGCTGCCTCCCTGGGACCTGTGGCCGCCTTCAAGGTGGCCACCCCCTACAGCCTCTACGTGT
GCCCCGAGGGCCAGAACGTCACCCTGACCTGCAGGCTGCTGGGACCCGTGGACAAGGGCCACGA
CGTGACCTTCTACAAGACCTGGTACAGGAGCAGCAGGGGCGAGGTGCAGACCTGCTCCGAGAGG
AGGCCCATCAGGAATCTGACATTCCAGGACCTGCACCTGCATCACGGCGGACACCAGGCTGCCA
ACACCAGCCACGACCTGGCTCAGAGGCACGGACTGGAGTCCGCCTCCGACCACCATGGCAACTT
CTCCATCACCATGAGGAACCTGACCCTGCTCGACAGCGGCCTGTACTGTTGCCTGGTGGTGGAGA
TCAGGCACCACCACAGCGAGCACAGAGTGCACGGCGCCATGGAGCTGCAGGTGCAGACCGGAAA
GGACGCCCCCTCCAACTGCGTGGTGTACCCCAGCTCCAGCCAGGAGAGCGAGAACATCACAGCC
GCTGCCCTGGCCACCGGAGCTTGTATCGTGGGAATCCTGTGCCTGCCCCTGATCCTGCTGCTGGTC
TACAAGCAGAGGCAGGCCGCCTCCAACAGGAGAGCCCAGGAGCTGGTCAGAATGGACTCCAACA
TCCAGGGCATCGAGAACCCCGGATTCGAAGCCAGCCCTCCTGCCCAGGGAATCCCTGAGGCCAA
GGTGAGGCACCCCCTGTCCTACGTGGCCCAGAGGCAGCCTAGCGAGAGCGGCAGACACCTGCTG
AGCGAACCTAGCACCCCTCTGTCCCCTCCCGGCCCTGGCGATGTGTTCTTTCCCAGCTTAGATCCT
GTGCCCGACTCCCCCAACTTCGAGGTCATCTGA Monkey VISTA                                                      (SEQ ID NO: 18)
ATGGGCGTGCCTACCGCCCCTGAGGCTGGATGTTGGAGGTGGGGTTCTCTGCTGTTCGCCCTGTTC
CTGGCTGCCAGCCTGGGACCTGTGGCCGCCTTCAAGGTGGCTACCCTGTACAGCCTGTACGTGTG
CCCCGAGGGCCAGAATGTGACACTGACCTGCAGAGTGTTCGGCCCCGTGGACAAGGGCCACGAC
GTGACCTTCTATAAGACCTGGTACAGGAGCAGCAGGGGCGAGGTCCAGACCTGCAGCGAAAGGA
GGCCCATTAGGAACCTGACCTTCCAGGACCTGCATCTGCACCATGGCGGCCACCAAGCCGCCAAC
ACCAGCCACGACCTCGCTCAGAGGCATGGCCTGGAGAGCGCCTCCGATCACCACGGCAACTTCA
GCATCACCATGAGAAACCTGACCCTCCTGGACAGCGGACTGTACTGCTGCCTGGTGGTGGAGATC
AGGCACCACCACAGCGAGCACAGAGTGCATGGCGCCATGGAACTCCAGGTGCAGACCGGCAAAG
ACGCCCCCTCCTGCGTGGCTTACCCCAGCAGCTCCCAGGAGAGCGAGAAGCAAGGGCCCTCC
AGCTGCCCCTTTTGGGTGATCTGCTCCCTGCTGAGCAGCAGCTGCACACAGACCCTGTTCGGAAC
ACTGGCCCTGAGCCCCCAGGCTCACAGGAATCCTAGCCCCCCCCCTCCCCTGCTGCTGCACATCC
CTAGCGCTAGCTCCCTGGTCCAGAGCCCCGAAGCCCACTCCCCTAGCATCTGCTCCGGCGTGAGC
GCTCCTCTGGCCAGCCTGGAGTGGCTGTGCCTGGGCAGCCATCTCTGGCTGGGCAAGGTGCCCCA
TGACAGGTACTGGGTGCCCCAGGCCGCTAAATGCTGCCCCTCCCATCAGCCTCCCATGACCTCCG TABLE 7-continued Sequences Description/Sequence/SEQ ID NO.

AGGGCTGGGGCAGCAGAATCCAGCTGCTGCAGATCAGCGTGTTTTGCGTCAGCGTGTTCCTGAGG
TGTTCCCTGCTGTGA

Mouse VISTA (SEQ ID NO: 19)
ATGGGCGTCCCTGCTGTGCCTGAAGCCAGCAGCCCCAGATGGGGAACCCTGCTGCTGGCTATTTT
CCTGGCCGCTAGCAGGGGCCTGGTGGCCGCCTTCAAGGTGACAACACCCTACAGCCTCTACGTGT
GCCCTGAGGGCCAGAACGCCACCCTGACCTGTAGGATTCTCGGCCCTGTGTCCAAGGGACACGAC
GTGACCATCTACAAGACCTGGTACCTGAGCAGCAGAGGGAGAGGTCCAGATGTGCAAGGAGCACA
GGCCCATCAGGAACTTCACCCTGCAGCACCTGCAGCATCACGGCTCCCACCTGAAGGCCAACGCT
AGCCACGACCAGCCCCAGAAGCATGGCCTGGAGCTGGCCAGCGACCACCACGGAAACTTCAGCA
TTACCCTGAGGAACGTGACCCCCAGGGACAGCGGACTGTACTGCTGCCTGGTGATCGAGCTGAA
GAACCACCACCCCGAGCAGAGATTCTACGGCAGCATGGAGCTGCAGGTGCAGGCCGGCAAAGGC
TCCGGTTCTACCTGTATGGCCAGCAACGAGCAGGACAGCGACAGCATCACAGCCGCTGCCCTGGC
CACAGGAGCCTGTATCGTGGGAATCCTGTGCCTGCCCCTGATCCTGCTGCTGGTGTACAAGCAGA
GGCAGGTGGCCTCCCATAGAAGAGCCCAGGAGCTGGTGAGGATGGACAGCAGCAACACCCAGG
GCATTGAAAATCCCGGCTTCGAGACCACACCCCCTTTCCAGGGCATGCCCGAGGCCAAGACAAG
ACCCCCCCTGAGCTACGTGGCCAGAGACAGCCCAGCGAGAGCGGCAGGTACCTGCTGTCCGAC
CCTAGCACACCCCTGAGCCCCCCTGGCCCTGGCGACGTGTTCTTTCCCAGCCTGGACCCCGTGCCT
GATAGCCCCAACTCCGAGGCCATCTGA Human VSIG3-hFc fusion protein (SEQ ID NO: 20)
ATGGGCTGGTCCTGTATCATCCTGTTCCTGGTGGCTACAGCCACAGGCGTGCATAGCCTGGAGGT
CTCCGAGTCCCCTGGCAGCATCCAAGTCGCCAGAGGACAGCCTGCCGTGCTGCCCTGTACCTTCA
CCACCAGCGCCGCCCTGATCAACCTGAACGTCATTTGGATGGTGACACCCCTCAGCAACGCCAAC
CAGCCCGAGCAAGTCATTCTGTACCAGGGCGGCCAGATGTTCGACGGAGCCCCCAGATTCCACG
GCAGGGTGGGATTTACAGGCACCATGCCCGCCACCAATGTGTCCATCTTCATCAATAATACACAG
CTGAGCGACACCGGCACCTACCAGTGTCTCGTGAACAACCTGCCCGACATTGGCGGCAGGAACA
TCGGCGTCACCGGCCTGACCGTGCTGGTGCCTCCTAGCGCCCCTCATTGTCAGATCCAGGGAAGC
CAGGACATTGGCTCCGACGTGATTCTGCTGTGCTCCAGCGAAGAGGGCATTCCGAGACCTACCTA
CCTGTGGGAGAAGCTCGACAATACACTGAAGCTGCCCTCCCACCGCCACCCAAGACCAAGTGCAG
GGCACAGTGACCATCAGGAACATCTCCGCCCTGAGCTCCGGACTGTACCAGTGTGTGGCCTCCAA
TGCCATCGGCACCAGCACCTGTCTGCTGGACCTGCAGGTCATCTCCCCCCAGCCCAGGAATATCG
GCCCTTGCCCCGCCCCCGAACTGCTGGGCGGCCCTAGCGTGTTCCTGTTCCCCCCCAAGCCCAAA
GACACCCTGATGATCAGCAGAACCCCCGAGGTCACCTGCGTGGTGGTGGATGTGTCCCACGAAG
ATCCTGAGGTGAAGTTCAACTGGTACGTCGACGGCGTGGAGGTGCACAACGCCAAGACAAAACC
CAGGGAGGAGCAGTACAACTCCACCTATAGGGTGGTCAGCGTGCTCACCGTCCTGCATCAGGACT
GGCTGAATGGCAAGGAATACAAGTGTAAGGTGTCCAACAAGGCCCTGCCCGCCCCCATCGAGAA
GACCATCAGCAAAGCCAAGGGCCAGCCTAGGGAGCCCCAAGTGTACACCCTGCCCCCCAGCAGG
GACGAGCTGACCAAAAACCAGGTGAGCCTGACATGCCTGGTGAAGGGCTTCTACCCCAGCGACA
TCGCCGTGGAGTGGGAGTCCAACGGCCAGCCTGAGAATAACTACAAGACCACCCCCCCTGTGCTC
GATTCCGACGGCAGCTTCTTCCTGTACAGCAAGCTGACAGTGGACAAATCCAGATGGCAGCAGG
GCAACGTGTTCAGCTGTTCCGTGATGCATGAGGCCCTGCACAACCACTATACCCAGAAGAGCCTG
AGCCTCTCCCCCGGCAAG SEQ ID NOs:1-16: amino acid sequence;
SEQ ID NOs:17-20: nucleotide sequence While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

We claim:

1. An isolated monoclonal antibody, or an antigen-binding portion thereof, comprising
   a heavy chain variable region comprising a CDR1 region, a CDR2 region and a CDR3 region, wherein the CDR1 region, the CDR2 region and the CDR3 region comprise amino acid sequences of SEQ ID NOs: 1, 2 and 3, respectively, and
   a light chain variable region comprising a CDR1 region, a CDR2 region and a CDR3 region, wherein the CDR1 region, the CDR2 region and the CDR3 region comprise amino acid sequences of SEQ ID NOs: 4, 5 and 6, respectively;
   wherein the antibody or antigen-binding portion thereof is able to bind V-domain Ig suppressor of T cell activation (VISTA).

2. The isolated monoclonal antibody, or the antigen-binding portion thereof, of claim 1, wherein the heavy chain variable region comprises an amino acid sequence set forth in any one of SEQ ID NOs:7-10.

3. The isolated monoclonal antibody, or the antigen-binding portion thereof, of claim 1, wherein the light chain variable region comprises an amino acid sequence set forth in any one of SEQ ID NOs: 11-14.

4. The isolated monoclonal antibody, or the antigen-binding portion thereof, of claim 1, wherein the heavy chain and the light chain variable regions comprise amino acid sequences set forth in (a) SEQ ID NOs: 7 and 11, respectively; (b) SEQ ID NOs: 8 and 12, respectively; (c) SEQ ID NOs: 9 and 13, respectively; (d) SEQ ID NOs: 9 and 14, respectively; (e) SEQ ID NOs: 10 and 13, respectively; or (f) SEQ ID NOs: 10 and 14, respectively.

5. The isolated monoclonal antibody, or an antigen-binding portion thereof, of claim 4, comprising a heavy chain constant region which is human IgG1 constant region, and a light chain constant region which is human kappa constant region.

6. The isolated monoclonal antibody, or an antigen-binding portion thereof, of claim 5, wherein the heavy chain constant region has the amino acid sequence set forth in SEQ ID NO:15, and the light chain constant region has the amino acid sequence set forth in SEQ ID NO:16.

7. The isolated monoclonal antibody, or the antigen-binding portion thereof, of claim 1, which (a) binds to human VISTA; (b) binds to monkey VISTA; (c) does not bind to mouse VISTA; (d) blocks VISTA-VSIG3 interaction; (e) promotes T cell activation; and (f) has in vivo anti-tumor effect.

8. The isolated monoclonal antibody, or the antigen-binding portion thereof, of claim 1, which is a mouse, human, chimeric or humanized antibody.

9. The isolated monoclonal antibody, or the antigen-binding portion thereof, of claim 1, which is an IgG1, IgG2 or IgG4 isotype.

10. A pharmaceutical composition comprising the isolated monoclonal antibody, or antigen-binding portion thereof, of claim 1, and a pharmaceutically acceptable carrier.

11. The pharmaceutical composition of claim 10, further comprising an anti-tumor agent and/or an antimicrobial agent.

12. A method for treating a cancer disease in a subject, comprising administering to the subject a therapeutically effective amount of the isolated monoclonal antibody, or the antigen-binding portion thereof, of claim 1 or the pharmaceutical composition of claim 11.

13. The method of claim 12, wherein the cancer disease is a solid or non-solid tumor.

14. The method of claim 13, wherein the cancer disease is selected from the group consisting of B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, and nasopharynx cancer.

15. The method of claim 12, further comprising administering an immunostimulatory antibody, a costimulatory antibody, a chemotherapeutic agent, and/or a cytokine.

16. The method of claim 15, wherein the immunostimulatory antibody is selected from the group consisting of an anti-PD-1 antibody, an anti-PD-L1 antibody, an anti-LAG-3 antibody, and an anti-CTLA antibody.

17. The method of claim 15, wherein the costimulatory antibody is an anti-CD137 antibody or an anti-GITR antibody.

18. The method of claim 15, wherein the chemotherapeutic agent is epitubicin, oxaliplatin, and/or 5-fluorouracil.

19. The method of claim 15, wherein the cytokine is GM-CSF and/or IL-4.

* * * * *